United States Patent [19]

Alderete

[11] Patent Number: 5,876,985
[45] Date of Patent: Mar. 2, 1999

[54] **METHODS AND COMPOSITIONS FOR THE PREPARATION OF RECOMBINANT *TRICHOMONAS VAGINALIS* PROTEINS AND PEPTIDES**

[75] Inventor: John F. Alderete, San Antonio, Tex.

[73] Assignee: Board of Regents, The University of Texas System, Austin, Tex.

[21] Appl. No.: 259,966

[22] Filed: Jun. 14, 1994

Related U.S. Application Data

[63] Continuation of Ser. No. 692,382, Apr. 25, 1991, abandoned.

[51] Int. Cl.[6] ........................... C12N 15/30; C12N 15/00; C12N 15/70; C07K 14/44
[52] U.S. Cl. ........................ 435/172.3; 435/6; 435/69.3; 435/252.3; 435/252.33; 435/320.1; 530/350; 536/23.5; 935/12; 935/27; 935/31; 935/73
[58] Field of Search .................................. 435/7.22, 69.1, 435/69.3, 252.3, 252.33, 320.1, 172.1; 530/403; 536/23.1, 23.5

[56] References Cited

U.S. PATENT DOCUMENTS

| | | | |
|---|---|---|---|
| 4,652,639 | 3/1987 | Stabinsky | 435/91.52 |
| 4,675,285 | 6/1987 | Clark et al. | 435/6 |
| 4,707,442 | 11/1987 | Alderete | 435/7 |
| 4,784,950 | 11/1988 | Hagen et al. | 435/68 |
| 4,859,464 | 8/1989 | D'Antonio | 424/88 |
| 4,906,742 | 3/1990 | Young et al. | 536/27 |
| 4,959,318 | 9/1990 | Foster et al. | 435/69.1 |
| 5,004,694 | 4/1991 | Moay et al. | 435/240.27 |
| 5,081,034 | 1/1992 | Bevilacqua et al. | 435/252.33 |

FOREIGN PATENT DOCUMENTS

| | | |
|---|---|---|
| 0141616 | 5/1985 | European Pat. Off. . |
| WO 86/02359 | 4/1986 | WIPO . |
| WO 87/02779 | 5/1987 | WIPO . |
| WO 87/06620 | 11/1987 | WIPO . |

OTHER PUBLICATIONS

Fortkamp, E., et al., DNA, vol. 5, No. 6, "Cloning and Expression in *Escherichia coli* of a Synthetic DNA for Aivudiz, The Blood Coagulation Inhibitor in The Leech", pp. 511–517, 1986.
Rubino et al., "Molecular Probe for Identification of *Trichomonas Vaginalis* DNA," *J. Clin. Microbiol.*, 29(4):702–706, 1991.
Alderete et al., ASM Annual Meeting, Anaheim, California, 13–17 May, 1990, Abstract, Category D–7.
Dailey & Alderete, ASM Annual Meeting, Anaheim, California, 13–17 May, 1990, Abstract, Category B–2.

(List continued on next page.)

*Primary Examiner*—Charles L. Patterson, Jr.
*Assistant Examiner*—William W. Moore
*Attorney, Agent, or Firm*—Arnold, White & Durkee

[57] ABSTRACT

Disclosed are methods and compositions for the recombinant preparation of *Trichomonas vaginalis* proteins and peptides, including recombinant DNA segments encoding such proteins or peptides. In particular, techniques are disclosed for the preparation of recombinant clones which comprise *T. vaginalis* DNA segments encoding proteins or peptides which are expressed essentially only in Type I or Type II isolates, such as protein P55, a protein which is uniquely expressed in Type II isolates. Additionally, techniques for the preparation of proteins or peptides encoding epitopes of protein P270 are disclosed, as well as a detailed characterization of the P270 protein based on the characterization of a recombinant clone encoding the epitope of the parent protein. The invention further discloses the fact that a protein, termed P230, is the immunodominant surface protein in which vaginal antibody is elicited in vaginitis associated with *T. vaginalis* infections, as well as techniques for preparing recombinant clones encoding such a protein. Associated aspects involve the application of immunological or hybridization based techniques involving one or more of the foregoing compositions.

21 Claims, 12 Drawing Sheets

```
  1  gaa  ttc  cGG GAT AAC GTT AGA AGT AAA GGA GTC ACA TTA GGC GCA GCA CAA CAA
  1            R   D   N   V   R   S   K   G   V   T   L   R   A   A   Q   Q 55  GGA CCA CCA TCC ATT AGC GAT TTT ACA ATA GAA GGT GGC ACA GAA CTG ACA ATT
 17   G   P   P   S   I   S   D   F   T   I   E   G   G   T   E   L   T   I 109  GGT AAT ACA TAT CCA ATC ACT ATC ACA CTT TCG CCA TCA TCA GAT TTA GCA GAT
 35   G   N   T   Y   P   I   T   I   T   L   S   P   S   S   D   L   A   D 163  TGC TTT TAT GCT TTC GAC ACA GAA ACT CAT CAT ACA TTC CCA GGT GAT GCT GCC
 53   C   F   Y   A   F   D   T   E   T   Q   H   Y   F   P   G   D   A   A 217  AGT AAA AGC CAG TGC ACA GAA CTA TTG GGT AAC TCT GAT AAA ACA GAG TAT ACA
 71   S   K   S   Q   C   T   E   L   L   G   N   S   D   K   T   E   Y   T
                       HindIII
271  GCC AAA TTA CAA GCT TCC GGT TCT GCA GGC AGT TTC AAT CTT TTC ATC CAA GTT
 89   A   K   L   Q   A   S   G   S   A   G   S   F   N   L   F   I   Q   V 325  GTT GAT AGA GAA GGT AGG GAT AAC GTT AGA AGT AAA GGA GTC ACA TTA CGC GCA
107   V   D   R   E   G   R   D   N   V   R   S   K   G   V   T   L   R   A
              EcoRI 379  GCA CAA CAA GGg  gaa  ttc
125   A   Q   Q   G
```

OTHER PUBLICATIONS

Alderete and Neale, "Relatedness of Structures of a Major Immunogen in *Trichomonas vaginalis* Isolates," *Infect. Immun.*, 57(6):1849–1853, 1989.

Chamberlain et al., "Genetic and Physicochemical Characterization of the Recombinant DNA–Derived 47–Kilodalton Surface Immunogen of *Treponema pallidum* subsp. pallidum," *Infect. Immun.*, 56(1):71–78, 1988.

Alderete et al., Phenotypes and Protein–Epitope Phenotypic Variation among Fresh Isolates of *Trichomonas vaginalis, Infect. Immun.*, 55(5):1037–1041, 1987.

Alderete et al., "Phenotypic Variation and Diversity among *Trichomonas vaginalis* Isolates and Correlation of Phenotype with Trichomonal Virulence Determinants," *Infect. Immun.*, 53(2):285–293, 1986.

Alderete et al., "Monoclonal Antibody to a Major Surface Glycoprotein Immunogen Differentiates Isolates and Subpopulations of *Trichomonas vaginalis,*" *Infect. Immun.*, 52(1):70–75, 1986.

Chang et al., "Monoclonal Antibodies Against *Trichomonas vaginalis,*" *Hybridoma*, 5(1):43–51, 1986.

Alderete et al., "*Trichomonas vaginalis*: Electrophoretic Analysis and Heterogeneity among Isolates Due to High–Molecular–Weight Trichomonad Proteins," *Exp. Parasit.*, 61:244–251, 1986.

Alderete et al., "Heterogeneity of *Trichomonas vaginalis* and Discrimination among Trichomonal Isolates and Subpopulations with Sera of Patients and Experimentally Infected Mice," *Infect. Immun.*, 49(3):463–468, 1985.

Torian et al., "Specific and Common Antigens of *Trichomonas vaginalis* Detected by Monoclonal Antibodies," *Infect. Immun.*, 43(1):270–275, 1984.

Alderete, Antigen Analysis of Several Pathogenic Strains of *Trichomonas vaginalis*, ([Infection and Immunity]) 39(3):1041–1047, 1983.

Dialog Search Report, May 15, 1990.

Alderete et al., "Vaginal antibody of patients with trichomoniasis is to a prominent surface immunogen of *Trichomonas vaginalis,*" *Genitourin Med.*, 67:220–225, 1991.

Alderete et al., "Vaginal Antibody of Patients with Trichomoniasis is to a Promonent Surface Immunogen of *Trichomonas vaginalis*," ASM Annual Meeting, May 5–9, 1991, Dallas, Texas, Abstract.

Alderete and Garza, "Identification and Properties of *Trichomonas vaginalis* Proteins Involved in Cytadherence," *Infect. and Immun.*, 56(1):28–33, 1988.

Alderete et al., "Specific Parasitism of Purified Vaginal Epithelial Cells by *Trichomonas vaginalis,*" *Infect. and Immun.*, 56(10):2558–2562, 1988.

Alderete, "*Trichomonas vaginalis* NYH286 Phenotypic Variation May Be Coordinated for a Repertoire of Trichomonad Surface Immunogens," *Infect. and Immun.*, 55(9):1957–1962, 1987.

Alderete and Kasmala, "Monoclonal Antibody to a Major Glycoprotein Immunogen Mediates Differential Complement–Independent Lysis of *Trichomonas vaginalis,*" *Infect. and Immun.*, 53(3):697–699, 1986.

Alderete et al., "Molecular analysis of *Trichomonas vaginalis* surface protein repertoires," *Molecular and Cell Biology of Sexually Transmitted Diseases*, Chapman & Hall, Boundary Row, London, publisher, David Wright and Leonard Archard, Ed., 1992.

Alderete, Identification of Immunogenic and Antibody–Binding Membrane Proteins of Pathogenic *Trichomonas vaginalis, Infect. and Immun.*, 40(1):284–291, 1983.

Arroyo et al., "Signalling of *Trichomonas vaginalis* for amoeboid transformation and adhesin synthesis follows cytoadherence," *Molecular Microbiology*, 7(2):299–309, 1993.

Arroyo et al., "Molecular basis of host epithelial cell recognition by *Trichomonas vaginalis,*" *Molecular Microbiology*, 6(7):853–862, 1992.

Batista et al., "Localization of Acetylated α–Tubulin in *Tritrichomonas foetus* and *Trichomonas vaginalis,*" *Cell Structure and Function*, 13:445–453, 1988.

Dailey and Alderete, "The Phenotypically Variable Surface Protein of *Trichomonas vaginalis* Has a Single, Tandemly Repeated Immunodominant Epitope," *Infect. and Immun.*, 59(6):2083–2088, 1991.

Dailey and Alderete, "Identification of the Tandemly Repeated, Immunodominant Epitope of the Phenotypically Varying Surface Protein of *Trichomonas vaginalis,* " ASM Annual Meeting, Dallas, Texas, May 5–9, 1991.

Desmond et al., "An ELISA Assay with a Monoclonal Antibody to all Geographic and Drug Resistant Strains of *Trichomonas vaginalis,*" *Federation Proceedings*, 42(4):855, Abstract 3300, 1983.

Khosnan and Alderete, "*Trichomonas vaginalis* with a Double–Stranded RNA Virus Has Upregulated Levels of Phenotypically Variable Immunogen mRNA," ([Journal of Virology]) 68(6):4035–4038, 1994.

Khoshnan and Alderete, "Multiple Double–Stranded RNA Segments Are Associated with Virus Particles Infecting *Trichomonas vaginalis,*" *Journal of Virology*, 67(12):6950–6955, 1993.

Krieger et al., "Inhibition of *Trichomonas vaginalis* Motility by Monoclonal Antibodies Is Associated with Reduced Adherence to HeLa Cell Monolayers," *Infect. and Immun.*, 58(6):1634–1639, 1990.

Lehker et al., "The Regulation by Iron of the Synthesis of Adhesins and Cytoadherence Levels in the Protozoan *Trichomonas vaginalis,*" *J. Exp. Med.*, 174:311–318, 1991.

Lehker et al., "Specific Erythrocyte Binding Is An Additional Nutrient Acquisition System For *Trichomonas Vaginalis,* " *J. Exp. Med.*, 171:2165–2170, 1990.

Mason and Gwanzura, "Reduced Lymphocyte Responses to Mitogens in Natural and Experimental Trichomoniasis," *Infect. and Immun.*, 58(11):3553–3557, 1990.

Musatovova et al., "Molecular Characterization of the AP65 Adhesion Protein Gene of *Trichomonas vaginalis*," 93rd General Meeting, Las Vegas, Nevada, Abstract, 1994.

Neale and Alderete, "Analysis of the Proteinases of Representative *Trichomonas vaginalis* Isolates, " *Infect. and Immun.*, 58(1):157–162, 1990.

Norgard et al., "Cloning and Expression of the Major 47–Kilodalton Surface Immunogen of *Treponema pallidum* in *Escherichia coli*,"([Infection and Immunity]) 54(2):500–506, 1986.

O'Brien et al., "The AP65 Adhesin of *Trichomonas vaginalis* Shows Homology to Conserved Domains of Dinucleotide Binding Proteins," 93rd General Meeting, Las Vegas, Nevada, Abstract, 1994.

Silva Filho et al., "Presence of laminin–binding proteins in trichomonads and their role in adhesion," *Proc. Natl. Acad. Sci, USA*, 85:8042–8046, 1988.

Song, Jun Ho, et al., *Journal of the Hanyang Medical College,* 11(1):199–210, 1991. English Abstract in provided on p. 210.

Torian et al., "cDNA sequence analysis of a 29–kDa cysteine–rich surface antigen of pathogenic *Entamoeba histolytica,*" *Proc. Natl. Acad. Sci. USA,* 87:6358–6362, 1990.

Torian et al., "Antigenic Heterogeneity in the 115,000 $M_r$ Major Surface Antigen of *Trichomonas vaginalis*[1]," *J. Protozool.,* 35(2):273–280, 1988.

Wang et al., "*Trichomonas Vaginalis* Phenotypic Variation Occurs Only Among Trichomonads Infected With The Double–Stranded RNA Virus," *J. Exp. Med.,* 166:142–150, 1987.

```
  1   gaa ttc cGG GAT AAC GTT AGA AGT AAA GGA GTC ACA TTA GGC GCA GCA CAA CAA
  1                R   D   N   V   R   S   K   G   V   T   L   R   A   A   Q   Q 55   GGA CCA CCA AAT ACA TAT TTT GAT AGC ATC ACA ATA CTT TTT ACA GGT GGC GCA GCA ATT
 17    G   P   P   N   T   Y   F   D   S   I   T   I   L   F   T   G   G   A   A   I 109   GGT AAT ACA TAT GCT TTC GAC ACT ATC CCA TCA TCG CCA TCA TCA TTA GAT GAT GCT GCA CTG
 35    G   N   T   Y   A   F   D   T   I   P   S   S   P   S   S   L   D   D   A   A   L 163   TGC TTT TAT GCT TTC GAC ACA ATC ACA GAA ACT CAT CAG TTC CCA GGT GAT TTA GAT
 53    C   F   Y   A   F   D   T   I   T   E   T   H   Q   F   P   G   D   L   D 217   AGT AAA AGC CAG TGC CAA GCT TCC ACA GAA CTA TTG GGT AAC TCT GAT AAA ACA GAG TAT ACA
 71    S   K   S   Q   C   Q   A   S   T   E   L   L   G   N   S   D   K   T   E   Y   T
                           HindIII 271   GCC AAA TTA CAA GAA GGT TCT GCA GGC AGT AGT TTC ATC CAA GTT
 89    A   K   L   Q   E   G   S   A   G   S   S   F   I   Q   V
                                EcoRI 325   GTT GAT AGA GAA GGT AGG GAT AAC GTT AGA AGT AAA GGA GTC ACA TTA CGC GCA
107    V   D   R   E   G   R   D   N   V   R   S   K   G   V   T   L   R   A 379   GCA CAA CAA GGg gaa ttc
125    A   Q   Q   G
```

METHODS AND COMPOSITIONS FOR THE PREPARATION OF RECOMBINANT *TRICHOMONAS VAGINALIS* PROTEINS AND PEPTIDES

This is a Continuing Application of application Ser. No. 07/692,382, filed Apr. 25, 1991 now abandoned.

The Government may own certain rights in the present invention pursuant to NIH/NIAID grant AI 22380, Project I.

BACKGROUND OF THE INVENTION

1. Field of the Invention

The present invention relates generally to genetic compositions and recombinant methodology from the preparation of *Trichomonas vaginalis* proteins and peptides, useful, e.g., in the detection, identification and characterization of *Trichomonas vaginalis* organisms, as well as in the development of vaccines.

2. Description of the Related Art

*Trichomonas vaginalis* remains one of the most poorly investigated infectious agents; yet it is the most prominent parasite causing an illness in developed countries. In all world societies trichomoniasis causes an economic and emotional burden equal to other devastating pathogens of microbial etiology.

Trichomoniasis is a non-self-limiting, gender-discriminating disease of women. Infection of men with *T. vaginalis* will mostly be asymptomatic and self-limiting. A major problem with this disease is the broad spectrum of symptomatology, ranging from asymptomatic carriers who are reservoirs for the parasite to patients with a foul-smelling bloody discharge, severe inflammation and discomfort. For reasons not known at present, asymptomatic women can become highly symptomatic, and host or parasite factors which help explain the susceptibility or resistance to *T. vaginalis* infection and/or trichomoniasis remain undefined.

The *Trichomonas vaginalis* parasite is a flagellated protozoan responsible for a world-wide sexually transmitted disease (Ackers, 1982; Honigberg, 1978; Krieger, 1981; Müller, 1983; Rein and Chapel, 1975). Yearly estimates of numbers of patients with trichomoniasis in the United States alone range from 4 million to as high as 10 million. Unfortunately, it is estimated that fifty percent of all patients will go undiagnosed using the standard procedure of visualization of wet-mount preparations (Spence et al., 1980). Alternative diagnostic methods, such as culturing of the parasite from vaginal swabs, are expensive, time consuming, and not readily available.

The differentiation among trichomonal isolates, based on pathogenicity levels inherent to individual isolates, have not been satisfactorily established (Krieger et al., 1990), even using rodent animal models (Honigberg et al., 1966) which do not mirror the human infection. This absence of an animal model remains a major impediment toward studying the extent and nature of sequelae caused by *T. vaginalis* parasitism. Recently, epidemiologic evidence points toward a possible predisposition of certain women with trichomoniasis for HIV infection (Laga et al., 1989; Laga et al., 1990). Finally, although nitroimidazoles used to treat trichomoniasis in humans are extremely efficacious, the drugs have toxic side-effects, and drug refractoriness by trichomonal isolates has been documented (Müller et al., 1980).

Independent investigations have demonstrated a dramatic variation in the antigenic structure of *T. vaginalis* isolated form patients (Krieger et al., 1985; Su-Lin et al., 1983; Teras, 1960). It has more recently been appreciated that the surface disposition of a repertoire of high molecular weight prominent immunogens may be responsible for some of this antigenic diversity (Alderete et al., 1985b; Alderete et al., 1986a; Alderete et al., 1987a). Through the application of immunological techniques, sera from patients with trichomoniasis have been classified as either Type I or Type II, depending on the presence or absence of various immunologic reactivities (Alderete et al., 1987b). For example, differential receptivity with an immunogen having a $M_r$ of ~270 (P270) is one means of distinguishing Type I and Type II isolates, with Type I isolates being a homogeneous population lacking P270 expression or their surface (Alderete et al., 1986c; Alderete et al., 1986d). So-called Type II isolates generally comprise a heterogeneous population with regard to surface expression of the P270 immunogen (Alderete 1987b).

Indirect immunofluorescence using the pooled patient sera demonstrated the heterogeneous nature of parental trichomonal populations (Alderete 1985b). Those isolates, which gave strong reactions by the whole cell-radioimmunoprecipitation assay (Alderete 1983b) mentioned above, were comprised of subpopulations of parasites in which some were fluorescent and some were non-fluorescent with the patient sera (Alderete et al., 1985b; Alderete 1987a). This earlier work also revealed the fascinating aspect of changing proportions of fluorescent and non-fluorescent parasites during in vitro cultivation, and this now required clarification.

The generation of monoclonal antibodies (MAbs) reactive to *T. vaginalis* surfaces was fortuitous, since one MAb (C20A3) gave cytofluorometric patterns among the various trichomonal isolates identical to those detected with the pooled sera from patients (Alderete et al., 1985b; 1986d; and 1987a). This MAb was a key reagent for confirming the property of protein phenotypic variation based on the surface expression of immunogens (Alderete et al., 1986c and 1987b), and the existence of two types of parental populations of *T. vaginalis* parasitizing humans was further demonstrated (Alderete et al., 1986c; 1986d; Alderete et al., 1987b).

Type I isolates are trichomonads that synthesize but do not undergo phenotypic variation for the surface expression of the immunogens. At the present time approximately 40% of women appear infected with Type I isolates. Type II isolates, then, are trichomonads capable of phenotypic variation. It is noteworthy that only ⅓ of women with Type II isolates harbor both fluorescent and non-fluorescent trichomonads in the vagina, but the numbers of fluorescent trichomonads are small in comparison to MAb non-fluorescent parasites (Alderete et al., 1987b). In other words, the in vivo environment apparently favors or selects for *T. vaginalis* organisms lacking the expression of the surface immunogen repertoire although upon in vitro cultivation the parasites readily revert to the opposite phenotype. This property was also in part experimentally demonstrated by showing the isolation of only non-fluorescent trichomonads after subcutaneous inoculation of mice hindquarters with only MAb C20A3-fluorescent parasites (Alderete 1987a). Nonetheless, the fact that 90% of women make antibody to the C20A3-reactive immunogen (Alderete et al., 1987b) showed the molecule was synthesized regardless of the Type or subpopulation designations of the infecting *T. vaginalis* isolate.

Of further interest is the delineation of three subpopulations of parasites among the Type II isolates (Alderete et al., 1986c). For example, in addition to the non-fluorescent organisms some, but not all, fluorescent trichomonads were readily killed in a complement-independent fashion after exposure to the C20A3 MAb (Alderete, 1986b). The lysis of some parasites expressing the C20A3-reactive immunogen might indicate an important biofunctionality for the molecule; however, *T. vaginalis* without surface immunogen are equally capable of in vitro and in vivo growth and multiplication.

The complexity of the surface immunogens with regard to antibody accessibility was further reinforced in these studies by the identification of another high molecular weight protein by a MAb called DM126. The protein was found on the surface of parasites of all isolates (Alderete et al., 1987b); however, flow cytofluorometry with DM126 again indicated the existence of homogeneous, non-fluorescent and heterogeneous populations as seen for the MAb C20A3. The accessibility of the immunogen to antibody binding was highly variable in spite of its presence on the trichomonal surface, indicating that conformational changes were occurring for this protein possibly depending upon the immediate microenvironment of the parasite. This property was termed epitope phenotypic variation.

More recently, the availability of monospecific antiserum to the purified immunogen has revealed the predominance of this molecule throughout trichomonal surfaces. Of particular interest, however, was the refractoriness of the parasites to complement-mediated killing in the presence of this monospecific antiserum. Although a precise chemical-molecular explanation for this property is unknown, it illustrates the overall resistance of the protozoan to killing by antibody against common, stable immunogens which might otherwise be targets for vaccine development strategies. These immune evasion capabilities certainly will allow the parasite to survive in the face of host antibody responses.

Curiously, Type II isolates predominate in vivo, a finding which suggests that Type II isolates may be more virulent. If this is the case, P270 may be an excellent molecular marker for virulent isolates. Importantly, the P270 immunogen elicits the highest levels of antibody in experimentally infected animals (Alderete et al., 1986d), and most, if not all, trichomoniasis patients make antibody to this molecule (Alderete et al., 1987b). The significance of the highly immunogenic nature of P270 and its role in host-parasite biology may prove important to an overall understanding of this major pathogen.

Other than the discovery of the P270 immunogen, little is known regarding the biology of *T. vaginalis* on a molecular level. Furthermore, very few molecular tools are presently available to the researcher or clinician which will allow the identification and characterization of *T. vaginalis* isolates. In particular, there are currently no reported methods for obtaining recombinant DNA agents for the direct identification and characterization of *T. vaginalis* isolates, or for use in producing *T. vaginalis* proteins or peptides, particularly antigenic or immunogenic proteins or peptides. Accordingly, there is currently a great need for recombinant methodology and genetic constructs which are applicable to *T. vaginalis*, particularly methodology directed to the identification of virulent isolates, or distinguishing between Type I and Type II isolates.

SUMMARY OF THE INVENTION

The present invention addresses one or more of the foregoing or other shortcomings in the prior art by providing recombinant technology applicable generally to the preparation of recombinant clones expressing proteins or peptides which include an antigenically reactive epitope of a *T. vaginalis* protein. The invention concerns DNA segments which encode a protein or peptide having one or more antigenically reactive *T. vaginalis* epitopes. As used herein, the term "antigenically reactive epitope" is intended to refer to an amino acid sequence of a protein or peptide which would correspond immunologically to an amino acid sequence found in a *T. vaginalis* protein, and which is thereby capable of being recognized by a monoclonal or polyclonal antibody prepared against the corresponding epitope of the *T. vaginalis* protein.

Particularly preferred will be DNA segments which encode a protein or peptide having an antigenically reactive epitope that is recognized by an antibody produced in response to a *T. vaginalis* vaginal infection. By way of example, one may mention *T. vaginalis* protein P230, in that this protein apparently stimulates an antibody response in connection with a *T. vaginalis* vaginal infection. In fact, the inventor has found that antibodies reactive with P230 comprise the principle antibody response to a *T. vaginalis* vaginal infection. Thus, DNA segments encoding one or more antigenic epitopes of P230 or, in fact, the entire protein, will find particular utility, for example in the preparation of peptide which may be employed in immunologically-based screening method.

In other aspects, the invention concerns DNA segments which encode a protein which undergoes phenotypic variation in a Type I or Type II *T. vaginalis* isolate, including peptides or variants of such a protein. As used herein, the phrase "phenotypic variation" is intended to refer to proteins which are expressed differentially in Type II as compared to Type I *T. vaginalis* isolates. Thus, a protein which undergoes phenotypic variation may be either a protein which is expressed in Type I isolate, but not in Type II isolates, or, alternatively, expressed in Type II but not in Type I isolates. It is contemplated that in order to achieve advantages in accordance with the present invention, one will not necessarily require DNA segments which encode the entire natural protein. Thus, DNA segments encoding portions or variants of such a protein, will find some advantages in accordance herewith. Accordingly, the term "peptide" is intended to refer to peptide sequences which are smaller than, or represent subfragments of, a naturally occurring protein, and yet which nonetheless exhibits utility in accordance herewith. Moreover, the term "variant" is intended to refer to an allelic variation, mutant, or genetically engineered protein or peptide which has been prepared based on a consideration of proteins disclosed herein.

A particular example of a protein which undergoes phenotypic variation in Type II *T. vaginalis* isolates is P270. The P270 protein has been previously characterized to a limited degree, based on analyses of *T. vaginalis* proteins. However, prior to now, there has been no recombinant means available to allow the preparation of the P270 protein, or epitopes thereof, in amounts adequate or sufficient to allow for their use, for example, in vaccines or immunologically-based assays. The present invention addresses these shortcomings by providing specific technology involving recombinant DNA cloning techniques, which allow the preparation and subsequent use of recombinantly produced P270 proteins or antigenic peptides thereof. Of particular significance is the production of a recombinant protein or peptide which represents the only epitope encoded by the P270 protein.

In other aspects, the present invention provides general techniques for the recombinant cloning of *T. vaginalis* proteins or peptides, particularly those which are differentially expressed essentially only in Type I or Type II *T. vaginalis* isolates. Such methods involve two steps. The first step includes preparing a recombinant clone bank or library comprised of individual colonies of recombinant host cells that include T. vaginalis DNA. Recombinant clone banks are prepared through the combination of T. vaginalis cDNA segments with an appropriate vector, and the subsequent recombinant vector used to transform or transfect appropriate host cells. The nature of the T. vaginalis DNA segments which are employed is not believed to be particularly crucial, so long as it is suited to the screening technique employed. Thus, it is contemplated that genomic T. vaginalis DNA fragments, cDNA, and even synthetic oligonucleotides are within the scope of the invention. Of course, the use of longer DNA segments will tend to encode larger peptides, perhaps having more than one epitope, whereas shorter segments will tend to encode shorter peptides, which may serve to "isolate" specific epitopes.

Where clone banks are to be screened by nucleic acid hybridization, the underlying DNA can be of virtually any derivation, as can the particular vector that is employed. Where expression screening is contemplated, though, a vector should be employed that is adapted for expression of the inserted T. vaginalis DNA segments. Moreover, the encoded T. vaginalis sequences should be capable of being expressed in the host employed. While it is believed that one may, where desired, employ eukaryotic host cells for the preparation of clone banks, where hybridization screening is contemplated it will generally be preferable to employ bacterial host cells. This is due to ease of preparation, manipulation, and the reduced time element involved in the construction and handling of prokaryotic clone banks. Particularly preferred for this aspect of the invention is the use of a bacteriophage, such as λgt10, that is specifically engineered for cloning cDNAs and screening with nucleic acid probes. Moreover, typical bacteriophage hosts, such as E. coli C600, allow for selection of only recombinant phage, thereby increasing efficiency of cDNA, isolation, and large plaque formation by the bacteriophage in this host is ideal for hybridization with nucleic acid probes. This bacteriophage also allows for preparation of high-titered recombinant clone banks more representative of expressed genes. However, there is no reason why this aspect of this invention cannot be practiced through the use of other techniques involving other phagemid vectors, such as pUC, pGEM3Z, pBluescript, etc.

After one has prepared a recombinant clone bank, in certain embodiments the bank is then screened by differential hybridization. In the case of λgt10, the phage will be plated out on a lawn of an appropriate host (e.g., E. coli C600), and duplicate lifts of the phage plaques will be prepared by placing nitrocellulose directly on the agar plaques for designated times. One lift will then be screened with a first probe set of nucleic acid sequences complementary to sequences expressed in Type II isolates, and the second probe set of nucleic acid sequences, complementary to sequences expressed in Type I isolates, will be used to hybridize with the duplicate lift.

As used herein, a probe set is intended to refer to a collection of probes comprising different nucleic acid sequences corresponding to the protein-encoding RNA complement of the particular T. vaginalis isolate, whether it be a Type I or Type II isolate. Most conveniently, DNA from individual colonies or bacteriophage plaques can be blotted directly onto a suitable support, such as a nitrocellulose filter or nylon membrane, then subjected to hybridization with probes. Then, by comparing the differential hybridization patterns achieved in each of duplicate blots made from the same DNA with the recombinant clone bank in employing these two different sets of probes, one can identify individual colonies which comprise a DNA segment encoding the protein expressed essentially only in a Type II T. vaginalis isolate and not in a Type I isolate, or vice versa.

The invention also contemplates that T. vaginalis clone banks can be screened by hybridization techniques to identify specific T. vaginalis genes, through the use of specific probes, such as oligonucleotides having sequences designed based on a consideration of the various embodiments disclosed herein. In general, it is believed that oligonucleotides as short as 10 to 12 bases in length can form sufficiently stable hybrids to be detectable, although larger sequences, such as 15 to 20, or even 25 or longer, will be preferred.

In still further embodiments, expression banks can be screened using anti-T. vaginalis antibodies, such as anti-P230 or P270 antibodies, as a means of identifying clones expressing antigen-encoding fragments. A convenient method for expression screening involves cloning the DNA into a suitable vector, such as λgt11, adsorbing of expression products onto a suitable support, such as nitrocellulose, nylon or similar materials, and screening with a selected antibody.

Lastly, after an appropriate clone or clones is identified, it is selected and cultivated under conditions appropriate to the circumstances. Thus, where the selected host is employed directly for expression of T. vaginalis peptides or proteins, it will be desirable to cultivate the cell under conditions favoring expression, including the inclusion of any needed transcription stimulators. However, when DNA characterization is desired, one may desire to employ conditions favoring replication of the cloned T. vaginalis sequences.

Through the application of the foregoing approaches, the inventor has successfully identified various recombinant genes. For example, a T. vaginalis DNA segment has been cloned which is found to encode a protein termed P55 of T. vaginalis which exhibits a molecular weight of about 55,000 daltons (55 kD). This protein is particularly useful because it is uniquely expressed only in the Type II isolates, which may be the more virulent form of the parasite; in which case, highly specific protein and antibody reagents can be made for diagnostic purposes.

In still further aspects, the present invention concerns methods for the detection of T. vaginalis antigens or antibodies in a biological sample. In general, these methods include obtaining a biological sample suspected of including one or more T. vaginalis antigens or antibodies, and testing the sample by immunological means for the presence of one or the other. As used herein, the phrase "biological sample" is intended to include any sample which is suspected of containing one or more T. vaginalis antigens or antibodies, and may include laboratory samples as well as clinical samples. In terms of clinical samples, the invention contemplates that T. vaginalis antigens or antibodies may be present, e.g. in vaginal exudates of infected females and in the urine of infected males. It is contemplated that a wide variety of immunological techniques will be applicable to this aspect of the invention, including RIA, ELISA, sandwich immunoassay, immunoprecipitation, immunoblot, and the like.

In still further aspects, the present invention contemplates a method for the detection of T. vaginalis nucleic acids in the sample comprising testing the sample by hybridization techniques for the presence of nucleic sequences therein which encode P55, P230 or P270 proteins or peptides. In a preferred embodiment, such a method involves adsorbing nucleic acids of the sample to a solid support, hybridizing the nucleic acid-adsorbed solid support with one or more gene probe segments of P55, P230 or P270 under conditions effective to promote specific hybridization, and detecting the formation of specific hybrids between the probe segments and sample by means of a label.

A typical solid support for carrying out such a detection method includes filters or membranes such as nitrocellulose, Zeta-probe membrane, nytran, or nylon-based filters. In terms of conditions effective to promote specific hybridization, it is proposed that the appropriate condition will be readily ascertainable by those of skill in the art in light of the disclosure herein. However, in general terms, appropriate conditions will include, e.g., hybridization at 42° C. in 50% formamide containing 5× SSC, 2.5× Denhardt's, 0.1% SDS, and 1 mM EDTA (Maniatis et al., 1982).

A variety of labels which can be employed for the detection of hybridization reactions are known in the art, and include enzyme labels such as horseradish peroxidase, alkaline phosphatase, avidin-biotin-based conjugates, and even radioactive labels.

In further aspects, the present invention concerns a kit for the detection of T. vaginalis antigens or antibodies, the kit including, alternatively, an antibody reactive with a P55 or P230 epitope, or a protein or peptide which includes a P55, P230 or P270 epitope, together with means for detecting a specific immunoreaction between an antibody and its corresponding antigen. Examples of suitable means include labels attached directly to the antigen or antibody, a secondary antibody having specificity for human Ig, protein A or even protein G.

In still further embodiments, the invention contemplates a kit for the detection of T. vaginalis nucleic acids in the sample, wherein the kit includes one or more nucleic acid probe specific for the P55, P230 or P270 gene, together with means for detecting a specific hybridization between such a probe and T. vaginalis nucleic acid, such as an associated label.

BRIEF DESCRIPTION OF THE DRAWINGS

FIG. 1A Confirmation that the recombinant protein encoded an epitope of P270 was obtained by immunoblot analysis of the autodegraded immunogen. The "ladder pattern" is obtained from the autodegradation of the P270 protein when a detergent extract of the parasite was incubated at 37° C. before electrophoresis and immunoblotting (Alderete and Neale, 1989). This is due to cysteine proteases of the parasite, which retain their activity under these conditions (Alderete and Neale, 1989). Identical patterns of reactivity were noted on blots treated with MAb C20A3 (lane 1) and rabbit antibody eluted from preparative phage plaques (lane 3). Preincubation of the blot with MAb totally competed with the binding of eluted rabbit antibody (lane 2). Blots were developed with alkaline phosphatase-conjugated goat anti-mouse (lane 1) or anti-rabbit (lanes 2 and 3) antibody. FIG. 1B The binding of antibody in pooled sera from patients to the autodigested P270 is shown in lane 1. Treatment of blots with either MAb (lane 2) or eluted rabbit antibody (lane 3) prior to incubation with the pooled patient sera as a source of anti-P270 antibodies totally inhibited binding of human serum antibody to autodegraded P270. An alkaline phosphatase-conjugated anti-human antibody was used as the probe to measure human antibody recognition of the blotted immunogen.

FIG. 2. Sequence and open reading frame of the cDNA encoding the immunodominant epitope of the P270 immunogen. Direct repeats of 49 nucleotides (bracketed region) encoding 17 amino acids flanked this cDNA sequence. The single letter code denoting the amino acids are listed below each codon. Nucleotides and amino acids are numbered at left. A HindIII restriction endonuclease site is present at nucleotide 281 (single underline). The amino acids sequence DREGRD (double underline) was predicted as having the greatest probability of forming an antigenic determinant.

FIG. 4A A single transcript complimentary to the cDNA probe was detected by Northern blot analysis of 10 μg of total RNA from T. vaginalis. FIG. 4B Southern blot analysis of restriction endonuclease digests of the trichomonal DNA suggest the gene is single copy. Approximately 5 μg of DNA was digested with EcoRI (E), HindIII (H) or SacI (S), electrophoresed on 1% agarose gels and blotted to Zeta-probe membranes. Hybridization was performed with the nick translated cDNA probe. FIG. 4C The tandemly repeated nature of the epitope sequence was demonstrated following limited digestion of trichomonal DNA with HindIII prior to hybridization with the cDNA probe. The DNA (5 μg) was restricted with 2 units of HindIII for increasing periods of time, electrophoresed on 1% agarose and analyzed by Southern blotting. HindIII was selected because the sequence recognized by this endonuclease is located in between the repeated segments of the cDNA (FIG. 2) and only a single band was hybridized by the cDNA in Southern blots of complete digests of the trichomonad DNA (FIG. 2B).

FIG. 5. Sequence of a HindIII-monomer of genomic DNA reactive with the cDNA probe (upper case letters). The open reading frame of this fragment was deduced from the sequence data in FIG. 2. The single letter code denoting the amino acids are listed below each codon. The epitope sequence, DREGRD, is double underlined, and the brackets show the 49 nucleotides that were repeated in the sequence data of FIG. 3. Lower case letters denote sequences immediately upstream and downstream of this gene segment. Confirmation that this 39 bp region is tandemly repeated in the gene for P270 was obtained by sequencing a larger (1.1 kb) cDNA encoding the MAb-binding epitope some of which is shown in lower case letters.

FIG. 8A illustrates Coomassie brilliant blue stained protein patterns of lysates of *E. coli* HB101 containing the pUC vector with the p1 cDNA insert, pJM-1, (lane 2). As a control, lysates of *E. coli* HB101 containing plasmid without a p1 insert were analyzed. One unique band with a $M_r$ of 55,000 was seen only in the *E. coli* harboring the recombinant plasmid (lane 2).

In FIG. 8B, duplicate gels, identical to those in part FIG. 8A, were blotted onto nitrocellulose and reacted with antiserum (Alderete, 1983a) to total *T. vaginalis* proteins. Antiserum was diluted 1:100 in PBS containing a 10% suspension of extract derived from French pressure cell lysis of control *E. coli* to adsorb nonspecifically reacting antibodies. As shown in part FIG. 8B only the nitrocellulose blotted with pJM-1 transformed *E. coli* reacted with anti-*T. vaginalis* serum. The 55-kDa protein was visualized when alkaline phosphatase-conjugated goat anti-rabbit IgG was added, followed by substrate. No similar reactivity was seen with control *E. coli* probed with antiserum. Control prebled rabbit serum did not yield a reaction with any proteins in the pJM transformed *E. coli*. Lane 3 presents an additional control to show the extensive reactivity of the antiserum to total trichomonad proteins, which were TCA (Trichloroacetic Acid) precipitated, electrophoresed, and blotted onto nitrocellulose.

In FIG. 8C, the specific expression of the protein in only the Type II representative isolate, NYH 286, was confirmed. Antibody was eluted from blots containing recombinant protein (lane 3, FIG. 8B) with 0.2M glycine, pH 2.8, dialyzed against PBS, and reacted with blots of total *T. vaginalis* proteins subjected to SDS-PAGE. As can be seen in FIG. 8C, only the type II, NYH 286, isolate (lane 2), but not the Type I, IR 78, isolate (lane 1), possessed a protein band detected by the antibody eluted from the recombinant protein in *E. coli* transformed with pJM-1.

Figures 6A, 6B:
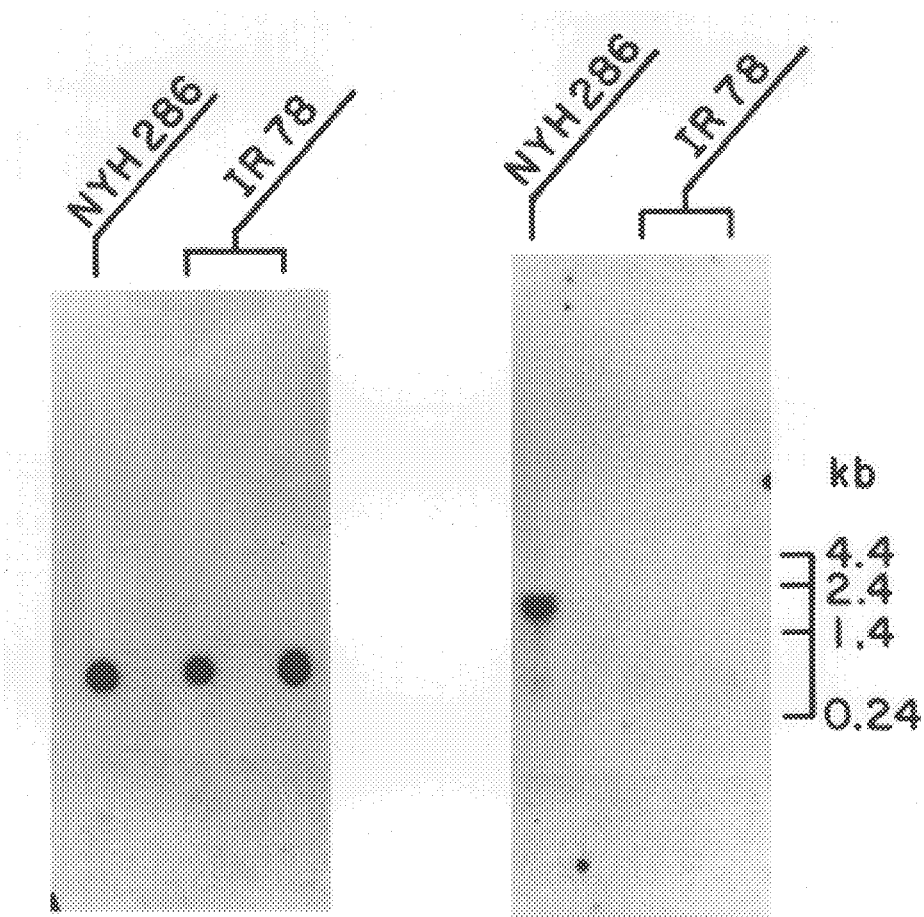
FIG. 6A and FIG. 6B. Northern blot analysis of total RNA from representative Type I (IR 78) and Type II (NYH 286) isolate of T. vaginalis using a cDNA hybridizing to mRNA of only the Type II, phenotypically varying isolates. The hybridization of 15 μg RNA from both isolates (lanes 1 and 2) and 75 μg RNA of isolate IR 78 (lane 3) was performed using a $^{32}$P-labeled cDNA, called p24, which reacted with both isolates (FIG. 6A) and with a $^{32}$P-labeled cDNA, called p1, uniquely reacting with only isolate NYH 286. The preparation of RNA was a previously described (Chirgwin et al., 1979). RNA was electrophoresed through a 1% agarose gel containing formaldehyde and blotted onto Nytran. Hybridization was for 18 hr at 42° C. Blots were washed in 0.1× SSC for 1 hr at 65° C. (Maniatis et al., 1982). Autoradiography was done for 24 hr at −70° C. with intensifying screens.

It is noteworthy that the presence of a protein in *T. vaginalis* with a $M_r$ identical to that expressed in the *E. coli* harboring the pJM-1 recombinant plasmid suggests that the cDNA is the entire structural gene for this protein. Also, the presence of the protein only in isolate NYH 286 (Type II) is consistent with the Northern analysis data (FIG. 6A and FIG. 6B above), indicating that the p1 cDNA originally isolated is uniquely expressed only among Type II isolates, capable of phenotypic variation.

Figure 9:

FIG. 9. Immunoreactivity of vaginal mucus antibody with surface proteins of *T. vaginalis*. Procedures for extracting antibody from mucus and for performing the immunoprecipitation (IP) assay with a detergent preparation of iodinated trichomonad surface proteins are as described in Materials and Methods. For these experiments *S. aureus* bacteria were pretreated with IgG fraction of goat anti-human IgG for adsorbing antibody in vaginal mucus extract. Control mucus refers to an IP reaction done identically but with mucus from a normal, uninfected human. The monoclonal antibodies (MAb) are also as described in Materials and Methods. Control refers to the specific reaction using an irrelevant MAb of isotype IgG2b that does not react with trichomonad surface proteins but which has the same isotype as DM126. A similar absence of reactivity by irrelevant MAbs with isotypes of the other MAbs (C20A3 and C55) was obtained.

Figure 10:
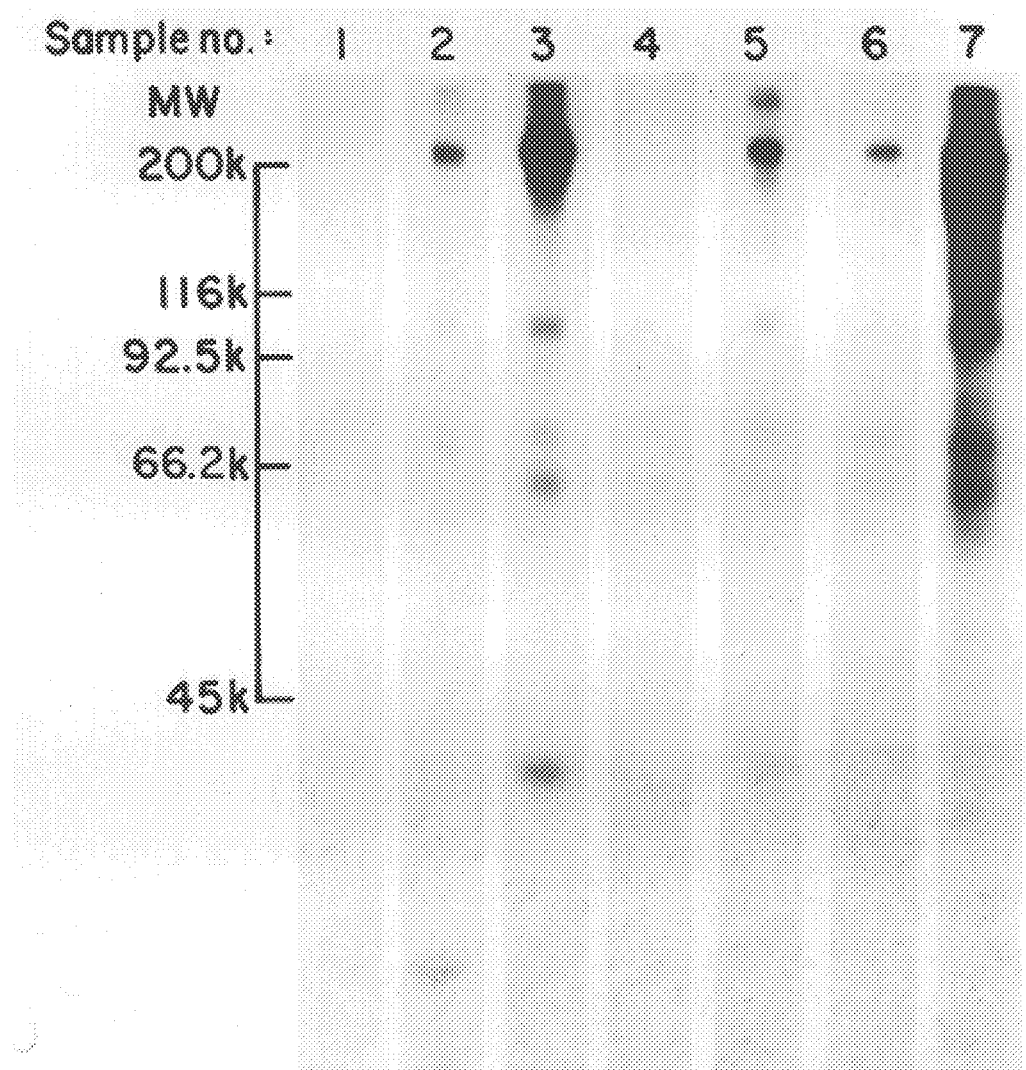

FIG. 10. Autoradiogram patterns showing the IP by antibody in some vaginal wash (VW) (lanes 2, 3, 5, 6 and 7) of a surface protein of *T. vaginalis*. *S. aureus* were first pretreated with IgG fraction of goat anti-human IgG before incubating with VW. The use of VW from normal, uninfected women in the IP assay gave similar absence of reactivity as did some patient VWs, like that seen for samples number 1 and 4, for example.

Figure 11:
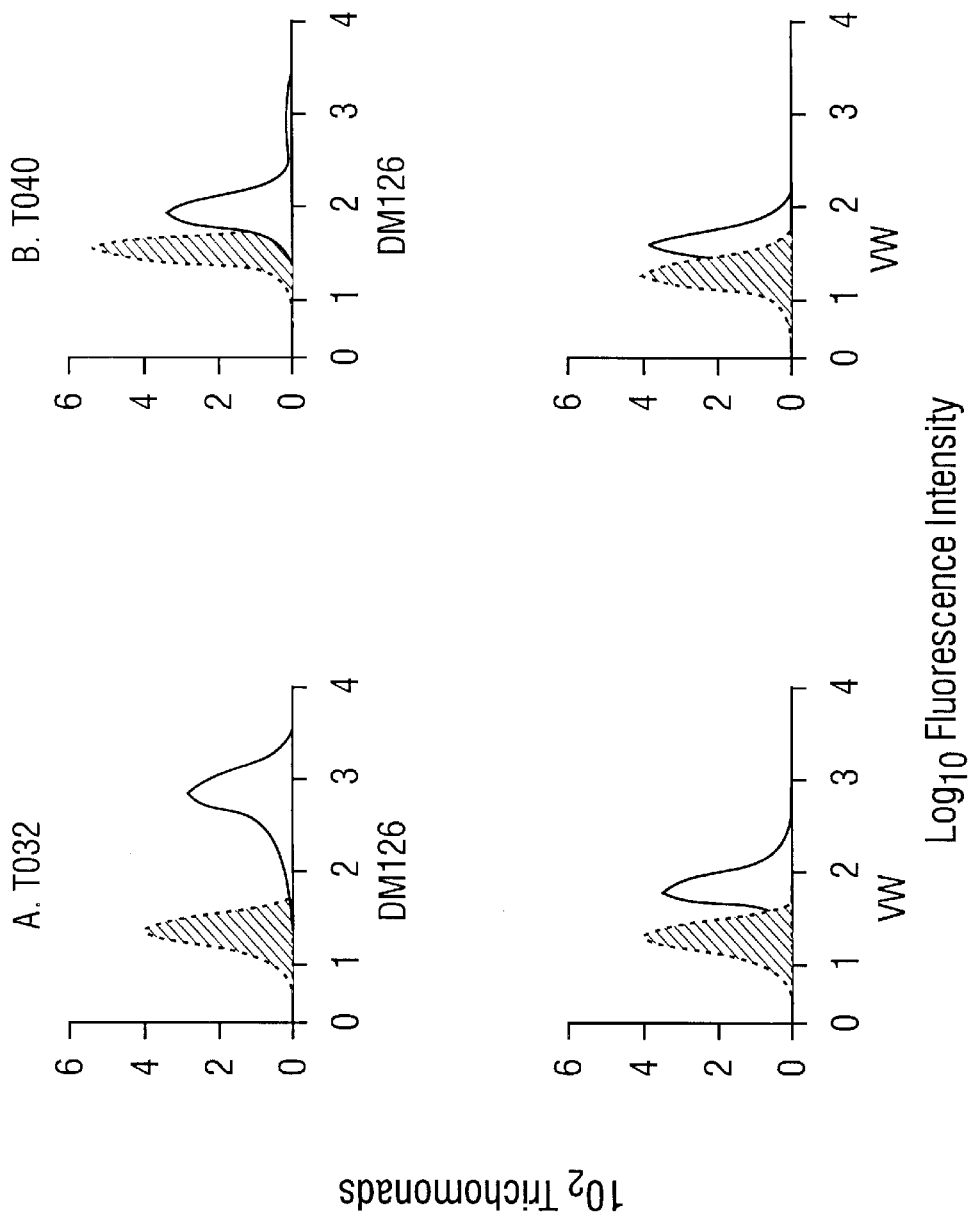

FIG. 11(A and B). Flow cytofluorometry patterns of two fresh isolates showing the VW Ab immunoreactivity with live trichomonads. Isolate T040 is representative of those which have been defined as Type I on the basis of phenotypic variation for the surface expression of the P270 immunogen as described in Materials and Methods and analyzed in FIG. 1A and FIG. 1B. Isolate T032 is defined as Type II, indicating an absence to undergo phenotypic variation for the P270 immunogen. These Type I isolates remain nonfluorescent during flow cytofluorometric analysis for MAb C20A3 reactivity. Note the different fluorescent patterns as seen by the D126 MAb in contrast to VW Ab, which gave heterogeneous fluorescent (solid lines) and non-fluorescent (lined areas) trichomonads. The dashed lines refer to the control reaction of parasites with irrelevant MAb for the DM126 experiment and with VW Ab from normal, uninfected women for the patient VW Ab experiment, respectively.

Figure 12:
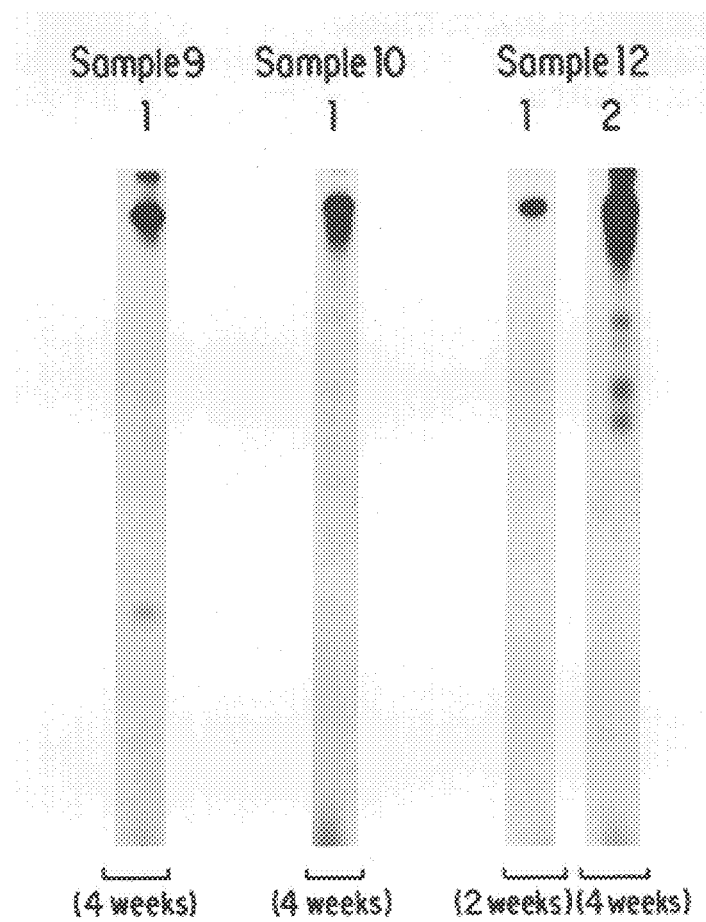

FIG. 12. Demonstration by the immunoprecipitation assay of the prolonged nature of the vaginal wash (VW) antibody response toward the P230 immunogen after treatment and cure of patients with trichomoniasis. The time after treatment when VW was obtained is indicated below each reaction. In this assay VW was mixed with a detergent extract of iodinated, surface-labeled trichomonads prior to precipitation of immune complexes with *S. aureus* bacteria. Antigen-antibody complexes were then solubilized by boiling in electrophoresis dissolving buffer prior to electrophoresis and autoradiography. No precipitation of iodinated proteins was seen with VW from control, uninfected women.

DETAILED DESCRIPTION OF THE PREFERRED EMBODIMENTS

I. Molecular Cloning of P270, A Phenotypic Variation Immunogen

The present inventor has found that the p270 immunogen has various attributes which make it an important target for the application of recombinant technology. Most notably, although the P270 immunogen is a large protein in terms of molecular weight, it nonetheless appears to include only a single immunogenic epitope. One basis for this conclusion is the fact that competition assays demonstrated that twenty distinct monoclonal antibodies against *T. vaginalis* all reacted with the same epitope (i.e., all monoclonals were capable of competing with each other for the same epitope). Similar results have been obtained using polyclonal antiserum, suggesting that the monospecific, polyclonal anti-P270 antiserum is in fact monoclonal, a somewhat surprising finding.

It has also been found that at least a portion of the p270 immunogen is composed of repeating units of the same sequence, wherein the repeating sequence corresponds generally to the single immunoreactive epitope.

A. Preparation of a cDNA Clone Encoding An Epitope of P270

Based on these discoveries, the applicant has proceeded to develop recombinant technology which will assist in the preparation of larger quantities of the p270 protein, or antigenic subpeptides, which can be employed, e.g., in immunodiagnostic assays or possibly as a vaccine. The approach taken to obtain a recombinant clone comprising p270 DNA involved the construction of an expression library in lambda phage, followed by screening of the library using an antibody having reactivity for P270. These studies are set forth in some detail below.

1. Materials and Methods
   a. Microorganisms

*T. vaginalis* NYH 286 undergoes phenotypic variation for surface expression of immunogens (Alderete et al., 1986c, 1987a and 1987b). Trichomonads were cultured in trypticase-yeast extract-maltose (TYM) medium supplemented with 10% heat-inactivated horse serum (Diamond, 1957). Nucleic acids and antigen analysis were performed on organisms grown for 20 h (Peterson et al., 1982).

*E. coli* strains TB1 and Y1090 were cultured in LB broth and ampicillin (100 μg/ml) added as needed (Maniatis et al., 1982).

b. Nucleic acid isolation from *T. vaginalis*

DNA from trichomonads lysed with 4M guanidinium thiocyanate was banded on CsCl gradients (Wang et al., 1985). DNA fractions were collected, dialyzed free of CsCl and precipitated by ethanol (Maniatis et al., 1982). For RNA, trichomonads were lysed in 4M guanidinium thiocyanate and the RNA collected by ultracentrifugation through a 5.7M CsCl cushion prepared in 0.1M EDTA (Chirgwin et al., 1979). The poly (A$^+$)RNA (mRNA) was purified from total cellular RNA by chromatography through poly-U Sephadex G-10 (Bio-Rad Laboratories, Richmond, Calif.) as described by the manufacturer. This purified mRNA contained no ribosomal RNA by electrophoresis analysis on agarose gels (Maniatis et al., 1982).

c. Electrophoresis and Hybridization

Samples were electrophoresed through 1% agarose in a 40 mM Tris-acetate buffer (Maniatis et al., 1982), and DNA bands visualized by staining with ethidium bromide (Maniatis et al., 1982).

Southern blot analysis was on samples electrophoresed on 1% agarose gels in 40 mM Tris-acetate buffer (Maniatis et al., 1982) and the DNA transferred to a Zeta-probe membrane (Bio-Rad Labs). Hybridizations with nick-translated cDNA (Maniatis et al., 1982) were performed at 42° C. in 50% formamide containing 5× SSC, 2.5× Denhardt's, 0.1% SDS, and 1 mM EDTA (Maniatis et al., 1982). The filters were then washed at 60° C. with 2× SSC/0.1% SDS followed by washing in 0.1× SSC/0.1% SDS at 60° C.

RNA was electrophoresed on 1% agarose/2.2M formaldehyde gels (Maniatis et al., 1982) and transferred to a Zeta-probe membrane in 40 mM NaOH as recommended by the manufacturer (Bio-Rad). Hybridization of the filter was as above.

d. Synthesis and cloning of a cDNA encoding the P270 epitope

Double stranded cDNA was prepared from 2 μg of trichomonad mRNA by the RNaseH method (cDNA Synthesis Kit, Boehringer-Mannheim (B-M), Indianapolis, Ind.) using the manufacturer's instructions. After the fill-in reaction, EcoRI-linkers were added for λgt11-cloning. The cDNA was then ligated into the bacteriophage vector λgt11, packaged using the Gigapack Gold packaging extracts (Stratagene, San Diego, Calif.), and plated on *E. coli* Y1090 cells (Maniatis et al., 1982).

Using standard procedures, a recombinant plaque was isolated following immunodetection with MAb C20A3, which is specific for the phenotypically varying P270 immunogen (Alderete et al., 1987b; Alderete et al., 1986c). The insert cDNA was purified from an EcoRI digest of the bacteriophage DNA and subcloned into the EcoRI site of pUC19. Recombinant plasmids were recovered following transformation of *E. coli* TB1 (Maniatis et al., 1982).

e. Purification of antibody from recombinant protein

Antibody bound to preparative plaques of recombinant bacteriophage on nitrocellulose was eluted with a solution of 0.2M glycine (pH 2.8), 0.2M NaCl and 0.1% bovine serum albumin. The eluted antibody solution was neutralized with 1M Tris-HCl and dialyzed against PBS.

f. Sequence analysis of the cDNA

The cDNA insert in pUC19 was sequenced by the double-stranded DNA sequencing technique ($T^7$sequencing Kit, Pharmacia, Piscataway, N.J.) using the Sequencing and Reverse sequencing primers (B-M). The λgt11 sequencing primers (B-M) were used to confirm the orientation and open reading frame of the insert DNA in the recombinant bacteriophage. The reaction products were visualized by electrophoresis on 6% polyacrylamide sequencing gels and autoradiography (Maniatis et al., 1982). The sequence was analyzed with the PC/GENE analysis software (IntelliGenetics, Inc., Mountain View, Calif.).

g. SDB-polyacrylamide gel electrophoresis and immunoblot analysis

Procedures for electrophoresis and immunoblot of *T. vaginalis* proteins have been described (Alderete et al., 1986).

2. Results a. Identification and initial characterization of a recombinant clone encoding an antigenic portion of P270

A high titered λgt11-cDNA library (~10$^6$ pfu) prepared as described above, was screened with MAb (C20A3) to P270. An immunoreactive plaque was isolated, and insert analysis of the bacteriophage DNA revealed the presence of a single insert of ~400 bp. Insert analysis of 5 μg of the recombinant phage DNA restricted with Eco RI showed the presence of a cDNA insert only in the λgt11phage reactive with the C20A3 MAb.

b. Expression of cDNA encoding the C20A3-reactive epitope of P270

The size of the recombinant protein containing the C20A3-reactive epitope was obtained by expression of the cDNA in the pIN-I vectors. The "A-series" of the plasmid expression vector was used to minimize the amount of bacterial protein fused to the recombinant trichomonad protein, thus getting a more accurate representation of the coding capacity of the cloned cDNA. These recombinant plasmids containing the cDNA were used to transform *E. coli* HB101 in order to analyze for the possible expression of the recombinant protein via a colony-probing enzyme immunoassay (Maniatis et al., 1982) using C20A3 or monospecific antiserum generated to the immunoaffinity-purified immunogen (Alderete et al., 1986, Alderete et al., 1987).

Protein extracts were prepared from 3 ml of an overnight broth culture of transformed *E. coli* containing the vector with the cDNA as well as from 3 ml of control *E. coli* containing the same vector without the cDNA insert. Solubilization of organisms was done by boiling in 300 μl of electrophoresis dissolving buffer (Laemmli et al., 1970). Insoluble material was removed by centrifugation, and 30 μl of extracts were electrophoresed by standard SDS-PAGE using 10% acrylamide separating gels and following electrophoresis, proteins were blotted onto nitrocellulose and probed with MAb C20A3 as previously described (Alderete et al., 1985, Alderete et al., 1986).

Immunoblot analysis of *E. coli* HB101 transformed with a recombinant pIN-I plasmid (lane 3) demonstrated the expression of a protein with a relative molecular weight ($M_r$) of ~15-KDa, which was detected with the C20A3 MAb. No similar detection of a protein was evident for control *E. coli* containing the same vector but without the cDNA. Demonstration of the reactivity of the MAb with the high $M_r$ protein in *T. vaginalis* total protein extracts has been shown previously (Alderete et al., 1986d).

c. P270 has a single tandemly repeated epitope

To further confirm that the cDNA encoded epitopes of the P270 immunogen, preparative plaques of the bacteriophage clone were first treated with monospecific anti-P270 serum. Antibody was eluted from the recombinant protein and then used in immunoblot analysis of trichomonad proteins. Earlier work had shown that limited autodegradation of P270 resulted in a "ladder pattern" of recognition by the MAb on immunoblots, which was distinctive for this protein (Alderete et al., 1989). The eluted rabbit antibody gave identical patterns of reactivity on immunoblots of the autodegraded immunogen as did MAb (FIG. 1A, lanes 1 and 3)(Alderete et al., 1989). Antibody prepared from similarly treated plaques of the bacteriophage vector lacking a cDNA insert failed to recognize P270, reaffirming that the cDNA encoded a portion of the P270 immunogen.

Figure 1A:
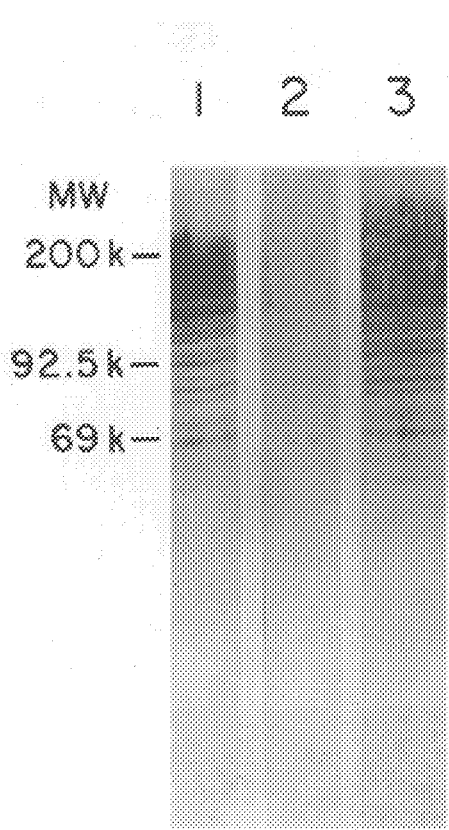
FIG. 1A and FIG. 1B. Demonstration that the recombinant bacteriophage clone encodes the single immunodominant epitope of P270.

Surprisingly, however, the eluted antibody only recognized a single epitope of P270, as demonstrated by a competition immunoblot experiment. Preincubation of the immunoblot with MAb totally inhibited the binding by the eluted rabbit antibody to P270 (FIG. 1A, lane 2). This abolishment of recognition by MAb of eluted antibody from rabbit antiserum to the parent P270 molecule suggested that the recombinant protein, $M_r$~14kDa, encoded only one epitope.

Figure 1B:
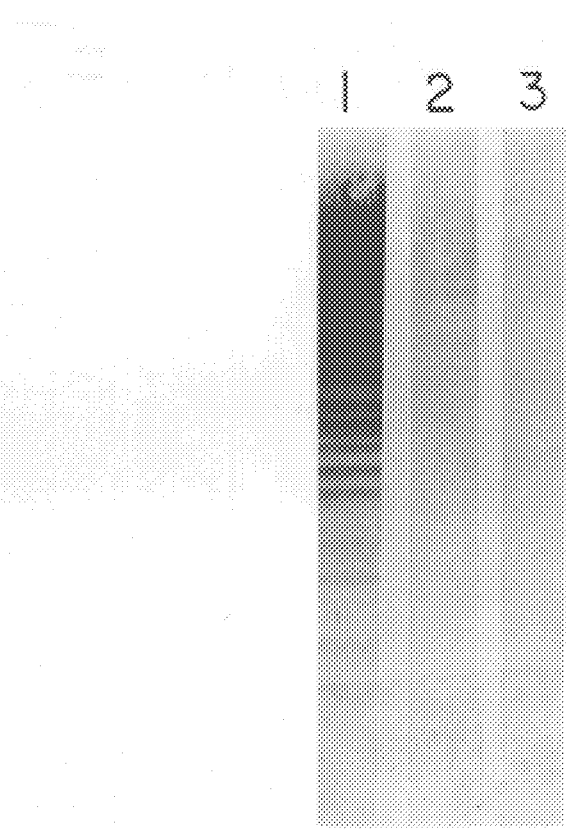

Similar blocking by the MAb and eluted rabbit antibody of recognition of P270 by anti-P270 antibody present in sera of patients with trichomoniasis was also observed (FIG. 1B). Lane 1 shows the characteristic multiple band pattern obtained on immunoblots of the autodegraded immunogen with the patient antibody. However, treatment of blots with either MAb (lane 2) or eluted rabbit antibody (lane 3) resulted in abolishment of patient antibody binding to P270. Identical inhibition results were obtained by MAb or eluted antibody of binding of monospecific antiserum to the parental P270 molecule. This shows that antibody in sera of patients is directed toward the single epitope of the recombinant protein and further reinforces the idea that the P270 molecule itself has only one immunodominant epitope. Control antibody preparations from the bacteriophage vector or MAb to an unrelated surface immunogen of *T. vaginalis* (Alderete et al., 1987b) did not interfere with patient antibody recognition of P270.

d. Characterization of P270 cDNA

The cDNA insert was then sequenced and the open reading frame encoding the recombinant protein determined (FIG. 2). The correct open reading frame was confirmed by sequencing the cDNA insert in the recombinant bacteriophage clone. The cDNA encodes for a protein of 14,218 molecular weight. Analysis of the DNA sequence revealed the presence of a 49 bp direct repeat (bracketed region) within the cDNA molecule (bases 8–56 on 5' side and 341–389 on 3' side), resulting in the reiteration of 17 amino acids in the recombinant protein.

Figure 3:
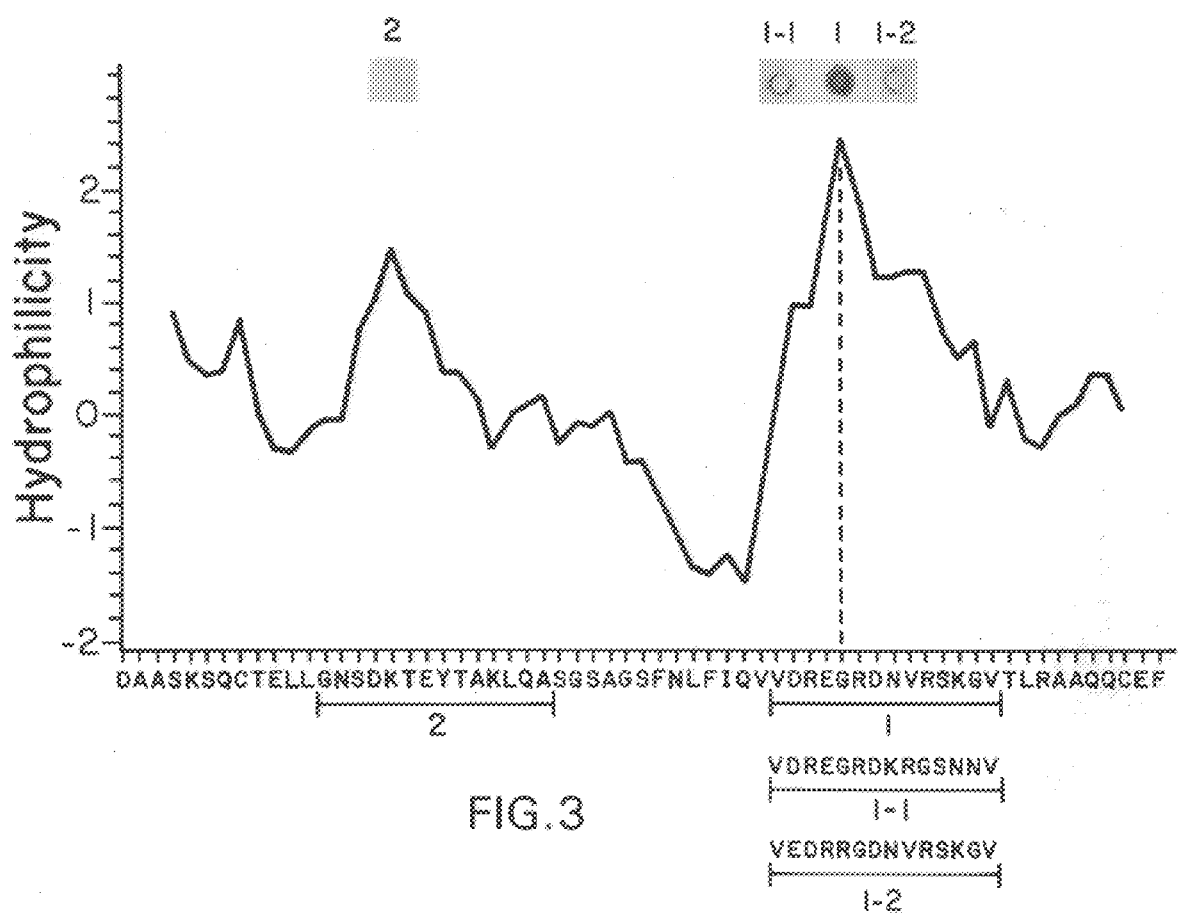
FIG. 3. Demonstration of the antigenic determinant recognized by the MAb. The hydrophilicity plot of the carboxy terminal region of the recombinant protein is shown with the corresponding single letter code denoting the amino acid. The peptide containing the putative DREGRD epitope sequence is denoted as "1" while other synthetic peptides with altered 5' and 3' ends of the peptide "1" sequence are noted as peptides 1-1 and 1-2, respectively. Synthetic peptides corresponding to the indicated sequences were purchased (Multiple Peptide Systems, San Diego, Calif.). A Bio-Dot apparatus (Bio-Rad Laboratories) was used to apply 400 μg of each peptide onto nitrocellulose and the blot treated with MAb by standard immunoblot procedures. The reactivity of the MAb with the peptides is displayed over the corresponding hydrophilic region on the graph.

The algorithm of Hopp and Woods (Hopp et al., 1981; and U.S. Pat. No. 4,554,101) identified the 6 amino acid sequence, DREGRD (FIG. 2, double underline), based on its hydrophilicity and probability of forming an antigenic determinant (FIG. 3). The 7 amino acids immediately downstream of the DREGRD sequence also contributed to the hydrophilicity of this region. Therefore, a 14 amino acid synthetic peptide containing the DREGRD core sequence plus one amino acid upstream and 7 amino acids downstream was synthesized. This peptide was shown by dot blot analysis to strongly bind the MAb (FIG. 3, peptide labeled 1). A control peptide synthesized to an unrelated hydrophilic region of the recombinant protein (amino acids 82–95, peptide 2) failed to bind MAb under the same conditions. Peptides with an altered DREGRD sequence (peptide 1-1) or with the 7 adjacent amino acids scrambled (peptide 1-2) demonstrated significantly lower levels of antibody binding, confirming the DREGRD specific sequence as the epitope for MAb recognition and also showed the importance of the downstream amino acids to the epitope.

Figures 4A, 4B, 4C:
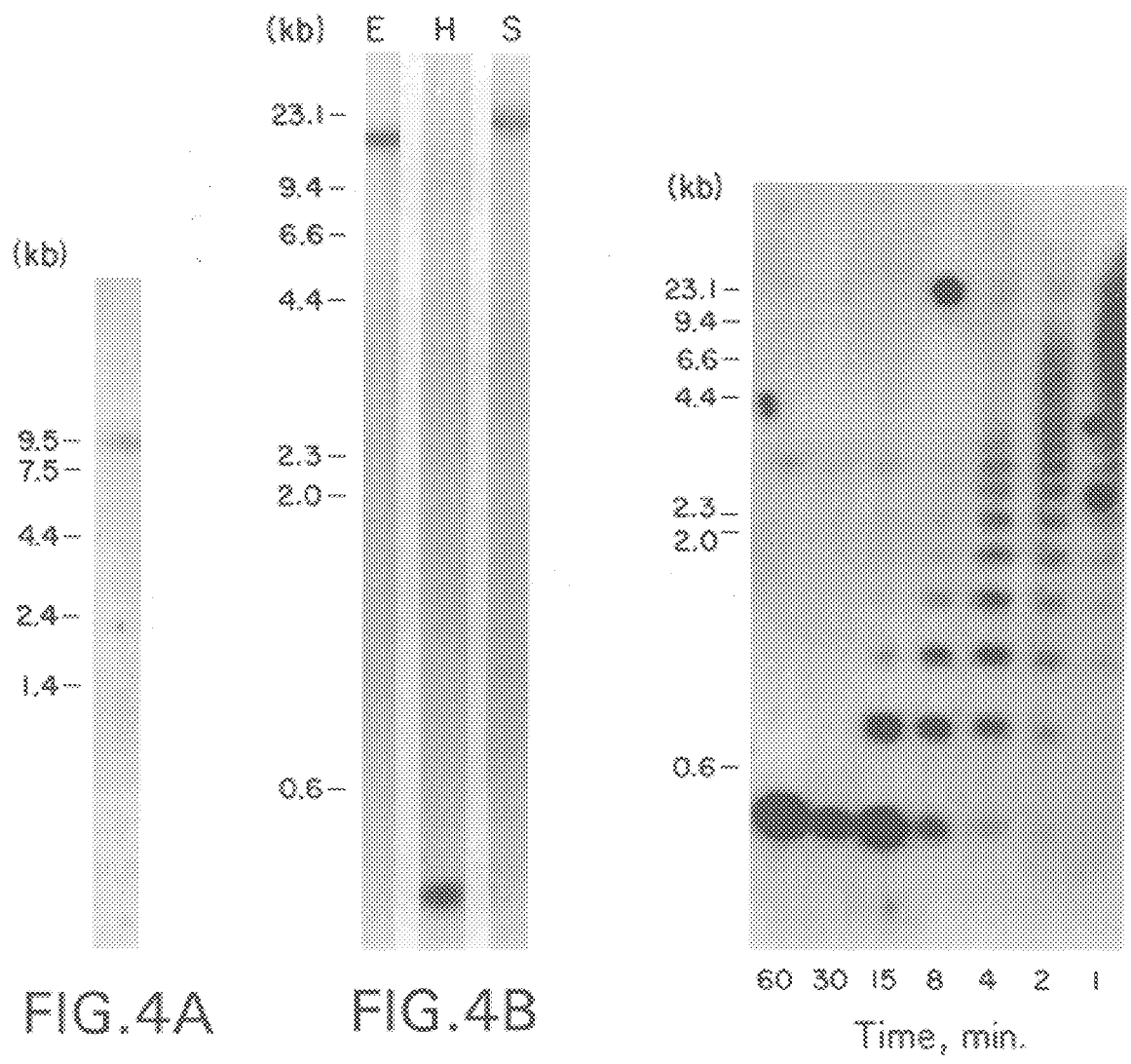
FIG. 4A, FIG. 4B, and FIG. 4C. Characterization of the gene encoding the P270 immunogen.

The genomic organization and expression of the gene encoding P270 were examined next by Northern and Southern blot analysis. A single transcript of ~9.5 kb, consistent with the size needed to encode for P270, was detected by the cDNA in RNA from the phenotypically varying isolate NYH286 (FIG. 4A). Southern blots of trichomonad DNA digested with several restriction endonucleases that do not cleave the cDNA sequence, such as EcoRI and SacI (FIG. 2), resulted in the hybridization of a single band, suggesting the gene's presence as a single copy in the parasite genome (FIG. 4B).

Figure 5:
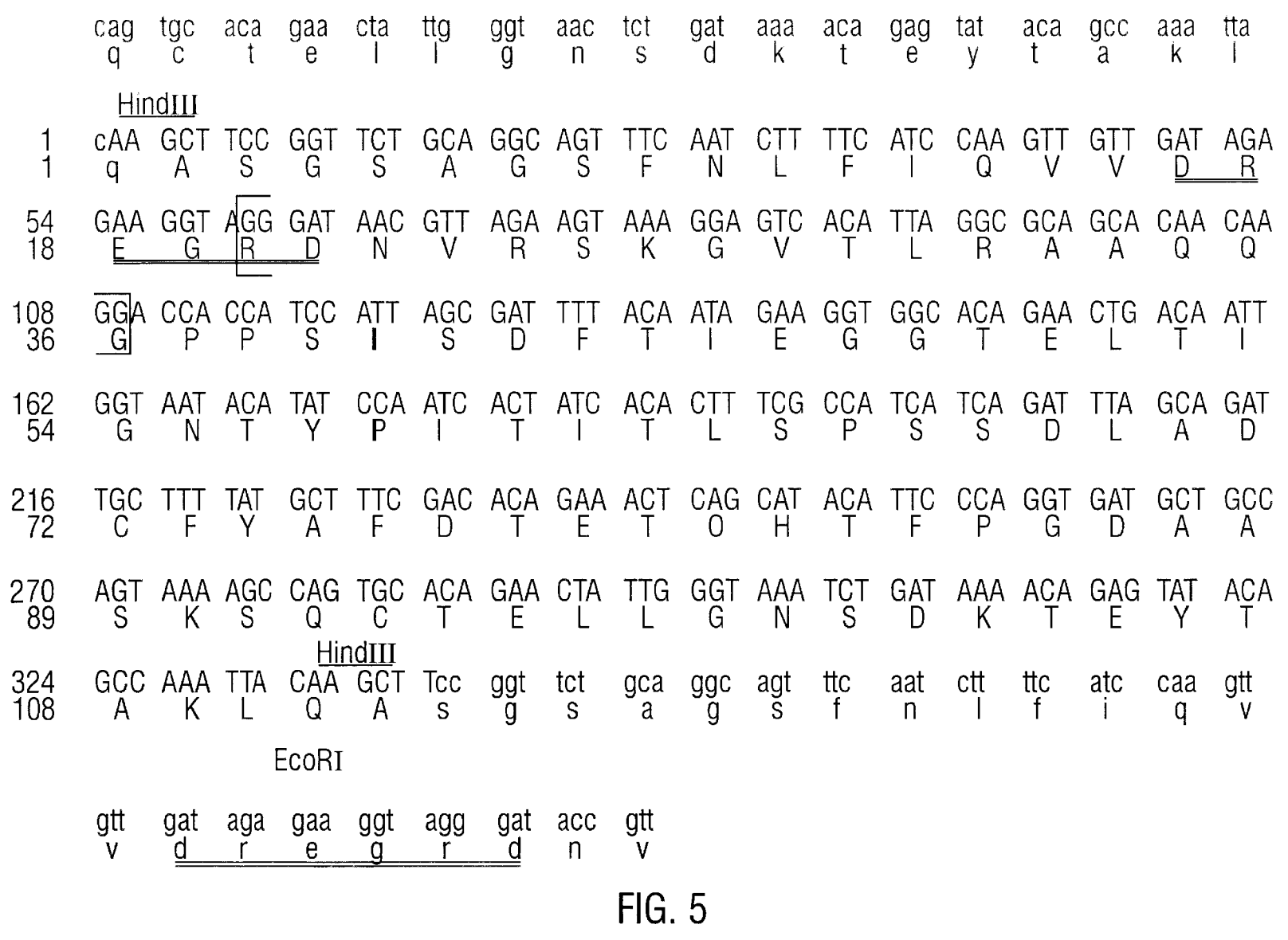

Finally, hybridization of HindIII digests of genomic DNA probed with the cDNA gave a single band of ~330 bp. This was surprising, since two bands were expected due to the HindIII site at position 281 in the cDNA (FIG. 2). Because the cDNA contains directly repeated sequences at the 5' and 3' termini (FIG. 2), it was hypothesized that genomic DNA was tandemly repeated. Indeed, a ladder pattern of recognition of DNA bands differing by ~330 bp was observed in a Southern blot analysis of partial HindIII-digested trichomonad DNA, demonstrating that the DNA sequence encoding the epitope was tandemly repeated at least 12 times (FIG. 4C). Therefore, a HindIII-monomer of the repeated sequence was cloned, and the protein encoded by this region was derived from the DNA sequence (FIG. 5). The sequence data matched that obtained earlier (FIG. 2), and the repeat element was 339 bp (the HindIII sites are labeled), encoding 112 amino acids for a protein of 11,700 molecular weight.

e. Isolation of Larger cDNA Copies of the Transcript Encoding P270

Attempts to isolate immunoreactive phage plaques from the λgt11-cDNA library resulted in the isolation of recombinant bacteriophage with cDNA inserts <400 bp. Therefore, a high titered λt10-cDNA library could be constructed from RNA of the same *T. vaginalis* isolate used earlier that is maximally expressing P270. Since the λgt10 vector does not express cloned insert DNAs, larger cDNAs may be more stable in this vector, facilitating their isolation.

A procedure for carrying out the synthesis of cDNA and generation of cDNA libraries using λgt11 and λgt10 is as follows:

*T. vaginalis* expressing high levels of the immunogen under investigation is an appropriate source of mRNA for preparation of complementary DNA (cDNA). The cDNAs are cloned into the bacteriophage vectors λgt11 and λgt10 as described by Huynh, et al. Studies using cDNAs prepared from mRNA of *T. vaginalis* NYH286 have resulted in cloning efficiencies of $1–3\times10^7$ recombinant plaque-forming units per/µg of cDNA for both vector systems.

Total cellular RNA can be prepared from *T. vaginalis* by lysis of the parasites in guanidinium thiocyanate followed by ultracentrifugation through a cesium chloride cushion as described by Chirgwin et al. (1979). Routinely, 8 mg of total cellular RNA having an $A_{260nm}/A_{280nm}$ ratio of 2.0 has been obtained from one liter broth cultures by this method.

Poly A+ RNA (mRNA) is conveniently isolated from 1 mg of purified cellular RNA by chromatography through poly (U)-Sephadex G-10 (Bethesda Research Laboratories, Bethesda, Md.) as described by the manufacturer. Poly(U)-Sephadex G-10 is preferably used because of the higher purity of mRNA when compared to oligo dT columns. Purified trichomonad mRNA, e.g., approximately 2 µg, is used to synthesize cDNA by the RNaseH method (cDNA Synthesis Kit, Boehringer-Mannheim, Inc., Indianapolis, Ind.). The ends of the newly made cDNA molecules are filled-in with T4 DNA polymerase and unphosphorylated EcoRI-linkers ligated to the resulting blunt ended cDNAs by T4 RNA and DNA ligases (Maniatis et al., 1982). The use of unphosphorylated linkers negates the need for methylation of the cDNA since EcoRI digestion is not to be needed to yield EcoRI cohesive ends on the cDNA. Instead, the linker-ligated cDNAs are incubated at 90° C. for 1 minute to dissociate the unligated complementary strand of the EcoRI-liner. The resulting cDNAs are sized and fragments >500 bp collected for subsequent cloning into the bacteriophage vector.

Sized cDNA fragments (100 ng) can be coprecipitated with 1 µg of bacteriophage vector DNA which has been previously restricted with EcoRI and the 5'-terminal phosphates removed by treatment with calf intestinal alkaline phosphatase (CIAP). Treatment of the DNA with CIAP results in less than 5% self ligation of the bacteriophage DNA. The precipitated DNAs can be ligated in a total volume of 5 µl with T4 DNA ligase at 15° C. for 16 hours (Huynh et al., 1985). After ligation, 20% of the ligated material can be packaged in vitro using the Gigapack gold packaging extracts of high efficiency (Stratagene, La Jolla, Calif.). *E. coli* strain Y1090 may be used for plaquing the λgt11 libraries. *E. coli* strain C600hfl is preferably used for the λgt10 libraries.

Clone banks bearing longer cDNA copies constructed as above may be screened using the partial clone described above.

Plaque lifts of the λgt10 cDNA library are prepared using nitrocellulose filters by standard procedures. The phage particles on the membrane are lysed by sequentially incubating the filters in a solution of 0.5M NaOH, 1.5M NaCl, 0.5M Tris, pH 7.5, and 1.5M NaCl, and 20× SSC. The filters are then baked in vacuo at 80° C. for 2 hr. The cDNA insert encoding the P270 epitope is radiolabeled by nick translation and used to probe the plaque lifts of the λgt10 library. Hybridization is typically performed at 42° C. in the presence of 50% formamide. The filters are then washed under stringent conditions at 65° C. and the reactive plaques identified by autoradiography. All reactive plaques are isolated, and the reactivity confirmed by rescreening. After plaque purification, phage stocks are prepared for DNA isolation and characterization.

1) Insert-analysis of recombinant phage clones

Bacteriophage purified from all reactive plaques are analyzed for the presence of cDNA inserts. Phage DNA is then prepared by standard procedures (Maniatis et al., 1982) and characterized by digestion with restriction endonuclease such as EcoRI, BamHI and HindIII. The resulting DNA fragments will be separated by agarose gel electrophoresis and visualized by staining with ethidium bromide and fluorescence with ultraviolet light. Restriction endonuclease digests of the vector DNAs will be included as controls to aid in the identification of cloned cDNA inserts.

2) Subcloning of the cDNA inserts from the recombinant bacteriophage

To facilitate further characterization of the cloned cDNAs, it will be important to subclone them into a plasmid vector such as pUC19 (Yanisch-Perron et al., 1985). The insert cDNA can be purified from EcoRI digests of the recombinant bacteriophage by electrophoresis of the digest on low melting point agarose gels. The isolated cDNA may then be ligated into the EcoRI site of pUC19 and then used to transform *E. coli* TB1 (Maniatis et al., 1982). Plasmid DNA is then isolated from transformants displaying a white phenotype by rapid extraction procedures (Maniatis et al., 1982) and analyzed for the presence of the cDNA insert by restriction endonuclease digestion and agarose gel electrophoresis. Glycerol stocks of the transformed *E. coli* cells and plasmid DNA stocks may be prepared for each recombinant clone.

3) Sequence analysis of the cloned cDNAs

The sequence of the cDNAs is important in defining the nucleotide composition of the repeat element as well as the corresponding amino acids comprising the antigenic determinant of the immunogen or at least the recombinant protein. The cDNA inserts may be sequenced by, e.g., the dsDNA sequencing technique ($^{77}$Sequencing Kit, Promega) using [$^{35}$S]dATP. The sequence reaction products can be separated by electrophoresis on 6% polyacrylamide sequencing gels and visualized by autoradiography (Bonner et al., 1974; Maniatis et al., 1982). Nucleotide and amino acid sequence analysis may be performed with the PC/GENE sequence analysis software (Intelligenetics, Inc).

4) Expression of the cloned cDNAs in *E. coli*

The cDNA inserts can be subcloned into the plasmid expression vector pIN-I (Masin et al., 1983) for immunochemical characterization of the recombinant protein. This expression vector system is preferred because it uses the strong, constitutive promoter from the lpp gene for expression of cloned insert DNAs. Furthermore, the "A-series" of the vector can be used to minimize the amount of bacterial protein fused to the recombinant protein. The vector also contains stop codons immediately downstream of the cloning site to prevent expression of plasmid sequences in the event the inserted DNA fails to encode them.

Expression of the cDNA inserts can be achieved by subcloning them into the EcoRI site of the pIN-I series of the plasmid vector. Recombinant plasmids can be used to transform *E. coli* HB101 (Maniatis et al.,1982) and screened for antigen expression via a colony-probing enzyme immunoassay (Maniatis et al.,1982). Transformants are replicate plated on grid plates and incubated overnight at 37° C. A nitrocellulose filter disk is then overlaid onto one of the plates and incubated an additional 30 min at room temperature. The colonies on the filter are lysed by sequentially incubating the filters on a series of three pads saturated with 0.1N NaOH, 1.5M Tris-HCl (pH 7.4), and 2× SSC, respectively. After air drying, the filter is baked at 80° C. for 2 hr and treated with the MAb C20A3 via standard immunoblotting procedures. All colonies showing color development should be retested to confirm reactivity. The identity of the recombinant protein is then confirmed from cell lysates of immunoreactive clones by SDS-PAGE and immunoblot analysis.

f. Construction of a Genomic Library of T. vaginalis and Isolation of the Structural Gene Construction of a genomic library is also important for further characterization of the gene structure in T. vaginalis. Furthermore, cloning of the genomic DNA would allow for the isolation of those sequences of the mRNA that for some reason are not efficiently copied into DNA.

A trichomonal genomic DNA library can be conveniently constructed in the lambda replacement vector EMBL4 (Maniatis et al., 1982). DNA may be extracted from T. vaginalis by standard procedures (Wang et al., 1985) and partially digested with an enzyme such as Sau3AI so as to maximize the production of 10–20 kb fragments (Maniatis et al., 1982). The digested DNA is then size-fractionated by centrifugation through a linear 10–40% sucrose gradient (Maniatis et al., 1982). Fractions containing DNA fragments between 10 and 20 kb in size are pooled and precipitated with alcohol.

The sized DNA can then be coprecipitated with the bacteriophage vector, which has been previously digested with BamHI and SalI. The precipitated DNAs, at a preferred vector/insert ratio of 3:1, are ligated and the reaction packaged as described previously for the construction of the cDNA libraries. E. coli strain NM539 can be used to amplify the library to minimize the presence of nonrecombinant. Recombinant bacteriophage harboring the trichomonad gene sequences are identified by the procedure described above for screening the λgt10-cDNA library.

Reactive plaques are purified and the insert DNA mapped by restriction endonuclease digestion and agarose gel electrophoresis. The epitope encoding cDNA can be used in Southern blot experiments of the restricted phage DNAs to map the location of the epitope segment. The sequences adjacent to the region recognized by the cDNA probe are subcloned and used as probes in Northern and Southern blots of trichomonal RNA and DNA, respectively, to localize the gene sequence. These sequences can also be cloned and expressed in the pIN-I vector system for future analysis of the protein separate from the immunodominant epitope.

II. Cloning of the Gene Specifically Expressed by the Type II Phenotypically Varying Isolates Isolates of T. vaginalis have been differentiated into two types based on the ability of trichomonads to undergo phenotypic variation. This was accomplished on the basis of reactions with the C20A3 MAb. Type I isolates were defined as stable and homogeneous, non-fluorescent trichomonads. In contrast, Type II isolates were populations containing both fluorescent and non-fluorescent parasites. Each of the trichomonads in this heterogeneous population was found to undergo phenotypic variation of surface expression of the immunogen detected by the C20A3 MAb.

Because recent data analyzing isolates from patients suggest that the phenotypically varying isolates predominate, indicating an important role for this property in virulence, and because isolates of T. vaginalis have been distinguished with respect to the surface expression of immunogens, the use of highly sensitive differential cDNA hybridization techniques was considered for isolation of cDNA clones of genes uniquely or abundantly expressed in the phenotypically varying trichomonads. Such a gene would be an attractive reagent for development of specific diagnostic and/or vaccine candidates.

A. The Ability to Establish cDNA Libraries in λgt10 for Performing Differential Hybridization Although it is possible to screen the λgt11 bacteriophage with nucleic acid probes, the efficient selection technique afforded by λgt10 for recombinant phage makes λgt10 especially attractive for differential hybridization. In addition, the large recombinant phage plaques are extremely useful for isolation of the important recombinant phage. Therefore, cDNA libraries were generated using mRNA from two distinct isolate types, as described above. In this way $^{32}$P-labeled first-strand DNA of a representative Type I and Type II isolate could be used for screening for a gene uniquely expressed in either Type I or Type II isolates.

B. Northern Blot Analysis Shows Expression of P1 Gene Only in Type II Isolates

Differential screening performed between a representative Type I isolate (IR 78) and Type II islotate (NYH 286) resulted in the identification of a full length cDNA, designated p1, that by Northern blot analysis was expressed only in the Type II isolate. For example, in FIG. 6B, the hybridization of 15 μg RNA from both isolates (lanes 1 and 2) and 75 μg RNA of isolate IR 78 (Type I)(lane 3) was performed first using a $^{32}$P-labeled cDNA, called p1, which reacted only with the isolate NYH 286, a Type II isolate. The faint band seen in all three lanes in part b was due to the incomplete removal of the p24 cDNA probe and also shows the different size of RNA detected by the two distinct cDNAs. Even longer exposure of the X-ray film did not detect any band with the p1 cDNA as probe on the blot containing 75 μg RNA (FIG. 6B, lane 3) from the Type I, IR 78, isolate.

The preparation of RNA was as previously described by Chirgwin, et al. (1979). RNA was denatured with formamide and electrophoresed through a 1% agarose/2.2M formaldehyde gel and blotted onto Nytran (Schleicher and Schuell, Keene, N.H.). Hybridization was for 18 hr at 42° C. in 50% formamide containing 5× SSC, 2.5× Denhardt's buffer, 0.1% SDS, and 1 mM EDTA (Maniatis et al., 1982). Blots were washed in 0.1× SSC/0.1% SDS for 2 hr at 65° C. (Maniatis et al., 1982). When needed, the probe was stripped form the filter by boiling in dH$_2$O and rinsed in 2× SSC prior to a second round of hybridization. Autoradiography was done for 24 hr at −70° C. with intensifying screens.

Figure 7:
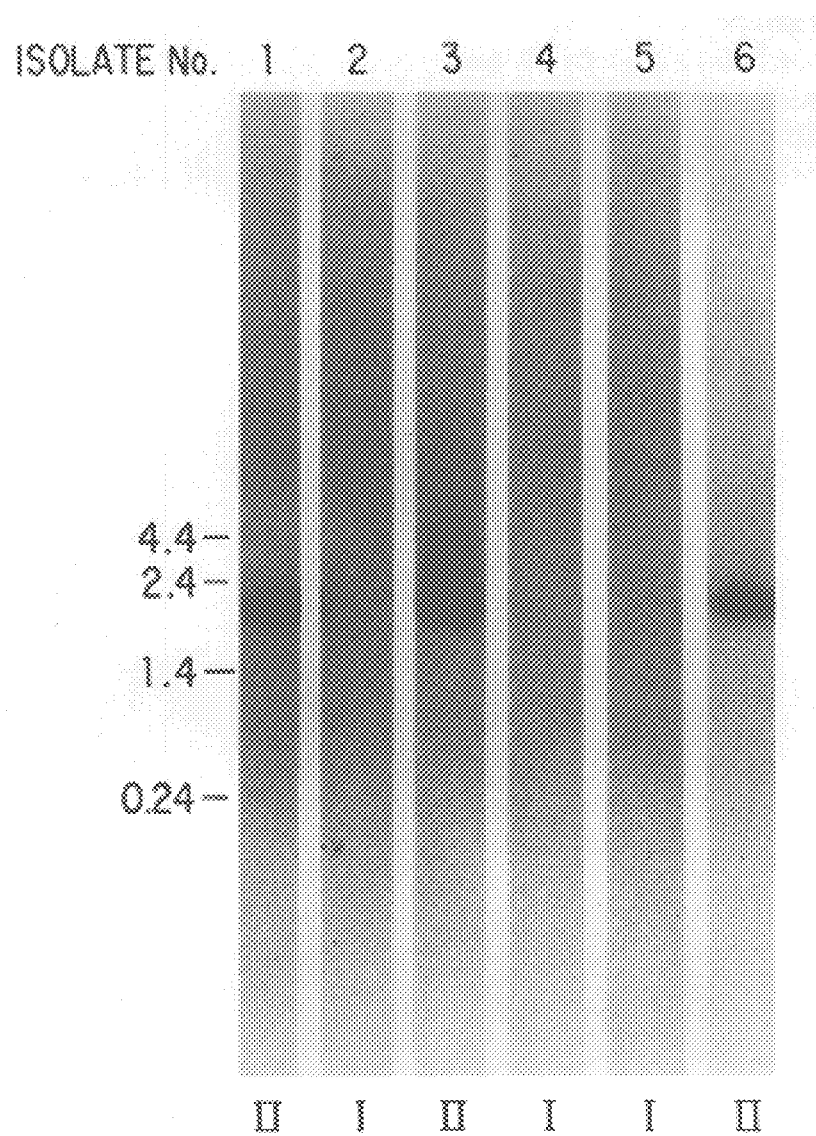
FIG. 7. Southern blot analysis of genomic DNA purified by an established procedure (wang et al., 1985) from several isolates of *T. vaginalis*. Representative isolates IR 78, T005, and T016-5 are Type I, while NYH 286, T018, and T022 are Type II. In this experiment 10 μg of DNA was first digested to completion with Eco RI and electrophoresed through 0.8% agarose before blotting onto Nytran. The blot was hybridized with $^{32}$P-labeled p1 cDNA shown in FIG. 6. After 18 hr at 42° C., the blot was washed with 0.1% SSC for 1 hr at 42° C. Autoradiography was performed as above (FIG. 6A and FIG. 6B).

It was important to test several isolates recently obtained from patients with trichomoniasis in order to confirm the specific expression of p1 cDNA in Type II isolates. Using conditions identical for those of FIG. 6A and FIG. 6B above, total RNA from eight fresh isolates was electrophoresed in 1% agarose containing formaldehyde and blotted onto Nytran. The autoradiogram of FIG. 7 presents results showing the reaction of $^{32}$P-labeled p1 cDNA with only Type II fresh isolates. Under identical conditions and even with prolonged exposure of X-ray film, the labeled p1 cDNA probe did not react with RNA from Type I isolates.

The blot was then boiled in dH$_2$O to release the radiolabeled p1 cDNA probe and rehybridized with the $^{32}$P-labeled p24 cDNA. Autoradiogram patterns using this probe as a control again showed the same intensity banding among all lanes, indicating the loading of similar amounts of total RNA for all isolates.

Parasites for fresh isolates were grown in vitro for $\leq 1$ week. Isolates were also cultivated for longer periods of time in order to insure that the isolate Type designations were accurate and that Type I trichomonads did not undergo phenotypic variation of the high $M_r$ immunogen detected with the C20A3 MAb. This was important because many fresh isolates can be homogeneous, non-fluorescent trichomonads initially, like those seen for Type I isolates; however, upon in vitro cultivation these organisms are capable of phenotypic variation. Therefore, all Type I isolates used for this study remained homogeneous, non-fluorescent throughout the cultivation period.

C. p1 cDNA Encodes for P55, a 55-kDa

Figure 8A:
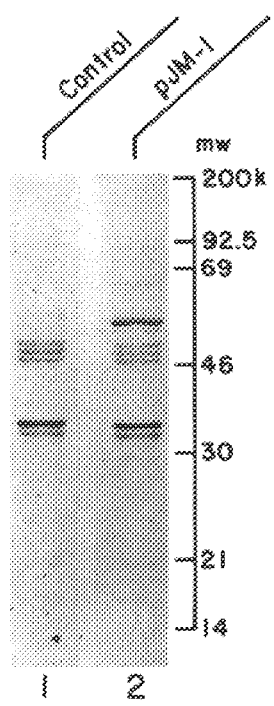
FIG. 8A, FIG. 8B, and FIG. 8C. The p1 cDNA encodes for P55, a 55-kDa protein. the p1 cDNA was subcloned into the pUC expression vector in order to attempt to produce a possible recombinant protein detectable in stained gels or by anti-*T. vaginalis* serum in immunoblots.

The p1 cDNA was subcloned into the pIN-I expression vector to produce a recombinant protein detectable in stained gels or by anti-*T. vaginalis* serum in immunoblots. FIG. 8A illustrates Coomassie brilliant blue stained protein patterns of lysates of *E. coli* HB101 containing the pIN-I vector with the p1 cDNA insert, pJM-1, (lane 2). As a control lysates of *E. coli* HB101 containing plasmid without insert were analyzed. Bacterial cell lysates were prepared and electrophoresed as described above. As can be seen one unique band with a $M_r$ of 55,000 was seen only in the *E. coli* harboring the recombinant plasmid (lane 2).

Figure 8B:
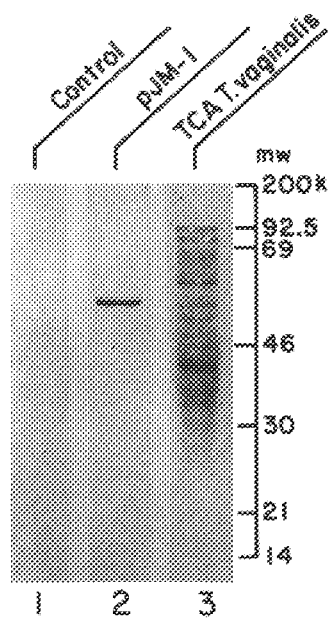

Identical, duplicate gels as seen in part A were blotted onto nitrocellulose and reacted with antiserum to total *T. vaginalis* proteins. Antiserum was diluted 1:100 in PBS containing a 10% suspension of extract derived from French pressure cell lysis of control *E. coli* to absorb nonspecifically reacting antibodies. As shown in FIG. 8B only the nitrocellulose blotted with pJM-1 transformed *E. coli* reacted with anti-*T. vaginalis* serum, and again, a 55-kDa protein was visualized when alkaline phosphatase-conjugated goat anti-rabbit IgG was added, followed by substrate. No similar reactivity was seen with control *E. coli* probed with antiserum. As expected, control prebleed rabbit serum did not yield a reaction with any proteins in the pJM-transformed *E. coli*. Lane 3 presents an additional control to show the extensive reactivity of the antiserum to total trichomonad proteins electrophoresed and blotted onto nitrocellulose.

Figure 8C:
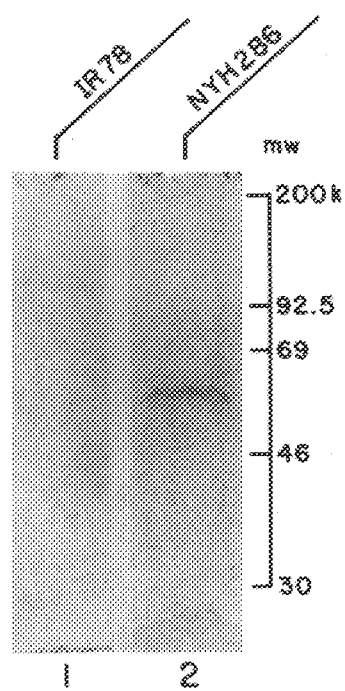

Finally, studies confirmed the specific expression of the protein in only the Type II representative isolate, NYH 286. Antibody was eluted from blots containing recombinant protein with 0.2M glycine, pH 2.8, dialyzed against PBS, and reacted with blots of total *T. vaginalis* proteins subjected to SDS-PAGE (Alderete, 1983a). As can be seen in FIG. 8C only the Type II NYH 286 isolate (lane 2), but not Type I IR 78 isolate (lane 1) possessed a protein band detected by the antibody eluted from the recombinant protein in *E. coli* transformed with pJM-1, as seen in part b.

It is noteworthy that the presence of a protein in *T. vaginalis* with a $M_r$ identical to that expressed in the *E. coli* harboring the pJM-1 recombinant plasmid suggests that the cDNA is the entire structural gene for this protein. Also, the presence of the protein only in isolate NYH286 is consistent with the Northern analysis data, indicating that the p1 cDNA originally isolated is uniquely expressed only among Type II isolates, capable of phenotypic variation.

D. Gene Copy Number and RFLPs for the P55 Gene

Moreover, data indicate that this is a multicopy gene present in all isolates, regardless of isolate Type designations. Although RFLPs are apparent for this gene among the different isolates, an individual RFLP does not correlate with the phenotypic variation among trichomonads. This observation indicated that transcription from this gene is controlled by a specific regulatory process and that the absence of transcriptional product in Type I isolates is not simply a result of spontaneous changes in the DNA observed through either mutations or recombinations. The factor(s) or condition(s) responsible for regulating the transcription of one or more of these gene copies is not known, but clearly, the multicopy nature of the gene is significant. It is interesting to hypothesize that differential expression of the multicopy genes in some isolates of *T. vaginalis* may be responsible for a new aspect of phenotypic variation that has yet to be reported for this or other pathogenic protozoa.

E. Antibody in Patient Serum to the P55 Recombinant Protein

Analysis of sera from a limited number of patients has indicated that approximately 50% of patients contain antibody to the P55-protein. This shows the in vivo relevance of the P55 protein, and the percentage is consistent with the percent of Type II-infected patients.

Through the continued analysis of additional patients, the prevalence of seroreactivity to this protein and a precise correlation with the infecting isolate type is determined. This is important to diagnosis or vaccine studies.

For these studies, immunoblots of preparative SDS-PAGE gels can be performed on the cloned recombinant protein. The region of the blot containing the recombinant P55-protein is excised and cut into small squares and incubated in a 1:10 dilution of individual serum from patients. Further treatment of the strips is conducted as for standard immunoblot experiments. Normal sera obtained from women with no record of trichomoniasis or sexually transmitted diseases are preferably included as negative controls. A rabbit antiserum prepared against the phenotypically varying isolate, *T. vaginalis* NYH286, and known to have antibody to P55, can serve as a positive control.

III. Biology of the P230 Immunogen That Undergoes Epitope Phenotypic Variation Another major high $M_r$ protein, termed P230, has been identified with the property termed epitope phenotypic variation. Two MAbs, designated DM126 and B1C20, have been generated to this immunogen. The 230-kDa protein immunogen, called P230, has been shown to reside on the surface of trichomonads at all times (Alderete et al., 1987b). This was demonstrated based on surface radioiodination; and the presence of the immunogen in purified membrane preparations, for example. Furthermore, the MAbs were able to bind their respective epitope; however, flow cytofluorometric analysis revealed changes in fluorescence patterns. In this case, fluorescence and non-fluorescence appears due to accessibility of the epitope to antibody binding.

Recent data indicates that this immunogen elicits an antibody response in the vagina of patients with trichomoniasis. Vaginal washes and mucus from ten patients possessed antibody immunoreactive with P230 (FIG. 9 and FIG. 10). This suggests a possible important role of this molecule at the site of infection. An intriguing and important finding based on fluorescence studies is the total absence of immunoreactivity by vaginal wash antibody with live parasites, indicating either a very restricted antigenicity of key epitopes on the molecule or immune evasion properties other than the phase variation represented by the P270 molecule. It is likely that continued investigation on this key immunogen will contribute to our understanding of the role of this protein to the biology of the host-parasite interaction.

A. Materials and Methods
1. Parasites and radiolabeling

Isolate NYH 286 and fresh clinical isolates, like T032 and T040, were used for experiments and were obtained as described by Alderete, 1987b. Trichomonads were passaged daily in a complex medium of trypticase-yeast extract-maltose supplemented with heat-inactivated horse serum (Diamond, 1957).

Surface radioiodination of washed, live organisms was performed using the chloramine-T iodination procedure, which has been described previously for efficient labeling of trichomonad surface proteins (Alderete et al., 1983b). Intrinsic labeling with [$^{35}$S]methionine was also as detailed by Alderete et al.(1983a), for preparation of detergent extracts for immunoprecipitation (IP) experiments as described below.

2. Vaginal Wash (VW) and Vaginal Mucus (VM)

VW was obtained using the procedure for isolation of vaginal epithelial cells (VECs; Alderete et al., 1988c), except that following low speed centrifugation of VECs, the VW was re-centrifuged at 17,500×g for 10 min to remove any remaining debris and bacteria. Finally, VW was passed through a 0.45 μfilter. Where needed, VWs of patients having Ab to the trichomonad immunogen were pooled or individually concentrated 10-fold by a rotary evaporator. VWs from normal, uninfected women were also processed similarly.

VM samples (~0.2 ml) recovered from patients using sterile tuberculin syringes with attached small diameter rubber tubing were mixed with 0.5 ml phosphate-buffered saline (PBS) containing standard penicillin-streptomycin for tissue culture. After overnight incubation at room temperature, the mucus was vortexed, and the insoluble mucus was removed by centrifugation. The PBS (~0.5 ml) containing soluble material, referred to as VM extract, was immediately filtered. This VM extract (0.4 ml) was then divided into two equal aliquots, and each aliquot was added to individual microfuge tubes containing a detergent preparation of radioiodinated or $^{35}$S-labeled trichomonads of isolate NYH 286, the common laboratory isolate used extensively for surface immunochemical characterization studies and known to contain the various prominent immunogens of *T. vaginalis*.

3. IP Assay

One hundred microliters of 10% (w/v) fixed *S. aureus* washed and suspended in 0.05% Zwittergent 3-12 (Z3-12) (Calbiochem-Behring, LaJolla, Calif.) in PBS was incubated with an equal volume of 1:200 dilution of the IgG fraction of goat anti-human IgG (Bio Rad Lbs, Richmond, Calif.) for up to two hours at 4° C. Alternatively, *S. aureus* was pretreated with IgG fraction of rabbit anti-human total Ig (Bio Rad). This washed, pretreated bacterial preparation was then incubated with VW. A 100 μl volume of this *S. aureus* suspension was then added to 200 μl of a detergent preparation of radiolabeled *T. vaginalis* (Alderete et al., 1988b). For the trichomonal preparation, ~2×10$^6$ radiolabeled trichomonads were solubilized in 1 ml of 0.05% final concentration Z3-12 prepared in PBS (Alderete et al., 1986d). Bacteria alone or pretreated with anti-human antibodies were also added to the trichomonal detergent preparation as controls. After extensive washing, the bacteria-antibody-antigen complex was boiled for 3 min in dissolving buffer for SDS-PAGE and subsequent autoradiographic detection of immunoprecipitated trichomonad proteins. All IP experiments were performed at least 3 times for VWs and twice for VM.

IP experiments were also performed using a MAb of isotype IgG$_{2b}$ called DM126 (Alderete et al., 1987b) that reacts with a M$_r$ 230-kDa (P230) trichomonad surface protein. This protein was distinguished from other surface proteins in IP experiments with MAbs that recognize a M$_r$ ~270-kDa protein (P270) (MAb C20A3, isotype IgG$_{2a}$) and a M$_r$ ~65-kDa protein (P65) (MAb C55, isotype IgG$_1$). Irrelevant MAbs were also employed as controls in order to show specificity in the assays.

In separate IP experiments the DM126 MAb-reactive immunogen was first depleted from the trichomonal detergent preparation by adsorption with *S. aureus* pretreated with DM126. This P230adsorbed detergent preparation, which still possessed P270 and P65 detectable with C20A3 and C55 MAbs, respectively, was used in the IP assay to show the specific anti-P230 response in the patient vaginal secretions.

4. Flow Cytofluorometry and Cytotoxicity of Live Parasites with MAB and VW antibody Indirect immunofluorescence monitored by flow cytofluorometry was performed with live trichomonads treated with MAb DM126 or VWs. Studies were also done to measure the cytolytic ability the MAb DM126 or VW Ab, and in this case the release of [$^3$H]thymidine-labeled DNA of live organisms was monitored (Alderete, et al., 1986b). Irrelevant MAbs of the same isotype but without reaction with live organisms served as negative controls.

B. Vaginal mucus from patients contains antibody to the P230 surface immunogen Mucus (~0.2 ml) recovered from patients using sterile tuberculin syringes with attached small diameter rubber tubing were mixed with 0.5 ml PBS and standard penicillin-streptomycin for tissue culture overnight. After vigorous vortexing, the insoluble mucus was removed by centrifugation, the PBS (~0.5 ml) containing soluble material was recovered and immediately filtered. The mucus "extract" (0.4 ml) of each patient was then added to individual tubes containing a detergent extract of radioiodinated trichomonads of isolate NYH 286, the common laboratory isolate used extensively for surface immunochemical characterization studies and known to contain the various prominent immunogens of *T. vaginalis* (Alderete et al., 1983b). The remaining 0.1 ml mucous "extract" was pooled for use in a separate experiment described below. The detergent and conditions used for preparation of extract for immunoprecipitation experiments were as previously published (Alderete et al., 1986d). Immune complexes were allowed to form overnight at 4° C. and were precipitated by protein A-bearing *S. aureus*. Radiolabeled antigens were then solubilized from the *S. aureus* bacteria by boiling in dissolving buffer, and electrophoresis was performed in 3% stacking and 7.5% separating acrylamide gels. Autoradiography was carried out to detect the trichomonad surface protein reactive by mucus antibody.

FIG. 9 shows the reaction of four representative mucus samples from patients with trichomoniasis (right side, lanes 2–4). All mucus samples from ten patients possessed antibody to one and possibly two iodinated proteins in the detergent extract. Mucus from a patient with sexually transmitted disease different from trichomoniasis was also processed similarly and did not possess any reactivity with iodinated trichomonad proteins. This absence of reactivity by individuals without trichomoniasis was further reinforced as described below using vaginal wash preparations.

A 230-kDa protein comigrated with a MAb called DM126 as well as with another MAb called B1C20. For example, as can also be seen in FIG. 9, experiments using these MAbs immunoprecipitated an iodinated protein with the same electrophoretic mobility as that seen by patient mucus, and this protein band was distinct from other proteins, such as P270 immunoprecipitated by C20A3 and a 65-kDa protein recognized by C55 MAb. The presence of irrelevant MAbs as controls and mucus from an uninfected individual did not immunoprecipitate any iodinated proteins from the extracts.

In a separate experiment the immunogen recognized by the DM126 MAb was removed from the detergent extract prior to incubation with patient mucus. This was done through exhaustive adsorption of trichomonal extract with *S. aureus* coated with DM126. This adsorbed extract still possessed the immunogens detectable by C20A3 and C55 MAbs but not by DM126, showing the specific removal of the DM126-reactive-protein from the detergent extract. A pooled mucus "extract" preparation was then added to adsorbed trichomonal extract. As can be seen in lane 1 of FIG. 10, it is noteworthy that antibody present in the patient mucus (lanes 2 through 4) now failed to immunoprecipitate the prominent immunogen. These data suggest that the primary immunogen in the urogenital-vaginal region to which patients make antibody is P230, the protein reactive with DM126 MAb.

The radioiodinated material which did not penetrate the 7.5% acrylamide gel in the immunoprecipitation assay with patient mucus (lanes 2–5) remains uncharacterized. It is possible that this represents a previously undescribed high $M_r$ protein immunogen of trichomonal surfaces. Alternatively, it is equally possible that the band represents aggregated protein reactive with DM126 MAb, since the band on top of the gel was also removed from the detergent extract adsorbed with DM126-pretreated *S. aureus*.

C. Vaginal washes (Vws) from patients have antibody to P230

The immunoreactivity of antibody in vaginal mucus with P230 prompted us to evaluate VWs obtained from patients as previously described (Alderete et al., 1984; Alderete et al., 1987b; Alderete et al., 1988c) for reactivity with the DM126-binding immunogen. VW was clarified of host cellular debris and microorganisms. Following centrifugation, 1 mM TLCK, a proteinase inhibitor, was added to VWs prior to filtering through 0.45 micron filters. The VWs (~2–4 ml) were then dialyzed against distilled water and concentrated to 1 ml. This concentrated VW was mixed with detergent extracts of radioiodinated trichomonads as previously described for RIP assays (Alderete et al., 1983b).

After overnight incubation at 4° C., immune complexes were precipitated with *S. aureus*, and radioiodinated, precipitated trichomonad proteins were processed as above for SDS-PAGE and autoradiography. FIG. 10 shows the presence of at least one band recognized by antibody present in VW of some patients. No similar reaction was seen with a pooled VW from normal women without a history of trichomoniases used as a control (lanes 1 and 4). The VW from patient number 2 was divided into two equal aliquots. For the second aliquot, no iodinated protein was immunoprecipitated under identical experimental conditions, except that the trichomonal detergent extract was first depleted of the 230-kDa protein through adsorption with DM126 MAb-coated *S. aureus* prior to use in the immunoprecipitation assay.

These data are consistent with that obtained using patient mucus. Further, the data indicate that the DM126 MAb-reactive immunogen is the primary surface protein recognized by the antibody present at the site of infection. Finally, the absence of other proteins following depletion of the extract for the 230-kDa protein indicates that the other minor bands seen on the autoradiogram are breakdown products of proteinase degradation. This is likely, since *T. vaginalis* cells possess numerous proteinases (Alderete and Neale, 1989; Coombs and North, 1983; and Lockwood et al., 1987), which have already been shown to degrade trichomonad proteins following solubilization in the detergents used for RIP assays (Alderete and Neale, 1989).

D. VW Ab shows heterogeneous populations by flow cytofluorometry

FIG. 1(A and B) shows patterns of fluorescence of duplicate preparations of trichomonads of two representative fresh isolates incubated with the DM126 MAb and with pooled VWs of patients. Isolate T032 was representative of a homogeneous immunoreactive population of fluorescent organisms with MAb DM126. Isolate T040, on the other hand, when probed with the MAb, subpopulations of both fluorescent and non-fluorescent organisms. The surface expression but MAb inaccessibility to epitope binding has been shown previously for the MAb-nonfluorescent parasites. Furthermore, changes in the ratio of fluorescent to nonfluorescent organisms seen during daily in vitro passage of the parasites, was indicative of epitope phenotypic variation.

Surprisingly, pooled VWs containing Ab to P230 detected only some, but not all, parasites in both isolates. The fact that VW antibody detected only a subpopulation in isolate T032, in contrast to the DM126 MAb, suggests a restricted antibody response to a P230 epitope different from that seen by the MAb.

E. VW Ab does not appear to kill immunoreactive trichomonads

Studies were performed to determine whether VW Ab mediated the cytolysis of organisms, as has been previously demonstrated using the MAb toward P270 (Alderete et al., 1986b). A 1 hr incubation at 37° C. with 7.5 µg/ml DM126 MAb, conditions which favored extensive agglutination of trichomonads of isolate T032, did not show release of [³H]thymidine-labeled DNA of live parasites. Exclusion of trypan blue, motility, based on flagella movement, and morphology were other visual indicators of parasite damage, and the trichomonads remained unaffected under these experimental conditions. VW was concentrated 10-fold and also caused antibody-mediated agglutination of parasites. The Ab mediated nature of agglutination was confirmed by first depleting VW of Ab by pretreatment with *S. aureus*, and the *S. aureus*-treated VW without Ab failed to agglutinate live organisms, even after addition of 10% guinea pig serum as a source of complement.

F. Ab to P230 does not immediately disappear following treatment of patients FIG. 12 shows the autoradiograms from the IP assay performed with VWs of three patients re-examined at later dates, as indicated. These VWs still had Ab to P230 following treatment. It was possible to obtain VW on more than one occasion after treatment, and these individuals had no evidence of a *T. vaginalis* infection at this time based on absence of parasites by microscopic and culture detection. The patient VWs still possessed Ab, and in the case of one patient (sample 12), VW obtained at four weeks possessed higher levels of reactivity to P230 than VW at 2 weeks. The reactivity was again demonstrated to be directed to only P230 by experiments using P230-adsorbed trichomonal detergent preparations, as previously mentioned.

G. Vaginal wash (VW) and MAb isolation of DNA sequence(s) expressing P230

Since this protein is common among all isolates of *T. vaginalis*, the purification of a DNA sequence encoding this protein will be useful for further studies. Several different methodologies may be employed for the isolation of P230. Initially, cDNA libraries such as those discussed in preceding sections will be screened using procedures appropriate to the vector as outlined below. If additional libraries are needed, they can be prepared as described below. It is believed that a molecular characterization of the gene sequence and corresponding P230 or immunoreactive protein fragments will be invaluable to understanding this important molecule and its significance to the overall parasite-host interrelationship. For example, the immune response of patients on the one hand and the immune evasion properties of *T. vaginalis* organisms on the other will be understood.

1) Screening of the λgt11-cDNa library for expression of P230 or immunoreactive peptides The bacteriophage λgt11 is a vector which expresses foreign DNA sequences as fusion proteins with β-galactosidase. Therefore, cDNA molecules that are cloned in the correct orientation and in the same reading frame as the β-galactosidase gene may be expressed in *E. coli* upon induction with isopropylthiogalactoside (IPTG). The λgt11-cDNA library may then be screened for trichomonad antigen expression utilizing established procedures. Phage particles are plated at a density of $5 \times 10^4$ pfu per 150 mm plate on the protease-deficient strain *E. coli* Y1090.

The expression of the β-galactosidase fusion proteins can be induced by overlaying each plate with a nitrocellulose filter disk saturated with 10 mM IPTG. Following plaque formation, the filters are removed and treated with the MAbs (DM126 and B1C20) reactive with P230. The highly reactive nature of VW with the P230 immunogen is also important for insuring the detection of highly significant recombinant proteins. The plaques expressing immunoreactive antigen are detected with alkaline phosphatase-conjugated secondary antibodies and stained for alkaline phosphatase activity (Alderete et al., 1984). All reactive plaques are isolated, their immunoreactivity confirmed and then plaque purified.

2) Screening of the λgt10-cDNA library.

Although it is believed that expression of immunoreactive clones can be obtained using λgt10, an alternative method for isolating cDNAs encoding immunoreactive epitopes of P230 may involve screening the λgt10 libraries. In this case, N-terminal amino acid sequence of the purified immunogen are preferably determined. Sufficient quantities of immunogen for amino acid sequencing are prepared using immunoaffinity columns (Alderete et al., 1987b). From this sequence information, the least degenerate oligonucleotide probe may be developed using the PC/Gene software which will specifically hybridize to the gene (mRNA) encoding the immunogen. The oligonucleotide probe is end-labeled with [$^{32}$P]γ-ATP using T4 polynucleotide kinase and hybridized to the DNA on the plaque lifts of the λgt10 library prepared as described above. Alternatively, small DNAs representing partial copies of the parent gene obtained from either the λgt11 library or the genomic library can be radiolabeled by nick translation and used to probe the plaque lifts of the λgt10 library. Standard hybridization procedures are followed in these procedures and reactive plaques identified by autoradiography (Maniatis et al., 1982). As with the λgt11 library all reactive plaques are isolated, their reactivity confirmed, and then plaque-purified.

IV. Associated Technologies

A. Nucleic Acid Hybridization Embodiments

As mentioned, in certain aspects, the DNA sequence information provided by the invention allows for the preparation of relatively short DNA (or RNA) sequences having the ability to specifically hybridize to *T. vaginalis* gene sequences. In these aspects, nucleic acid probes of an appropriate length are prepared based on a consideration of the sequence, e.g., as shown in FIG. 2, or that comprised within the p1 cDNA, or derived from flanking regions of these genes. The ability of such nucleic acid probes to specifically hybridize to the *T. vaginalis* gene sequences lend them particular utility in a variety of embodiments. Most importantly, the probes can be used in a variety of diagnostic assays for detecting the presence of pathogenic organisms in a given sample. However, either uses are envisioned, including the use of the sequence information for the preparation of mutant species primers, or primers for use in preparing other genetic constructs.

To provide certain of the advantages in accordance with the invention, the preferred nucleic acid sequence employed for hybridization studies or assays includes sequences that are complementary to at least a 10 to 20, or so, nucleotide stretch of the selected sequence, such as that shown in FIG. 2. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. Thus, one will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

The present invention will find particular utility as the basis for diagnostic hybridization assays for detecting trichomonal-specific RNA or DNA in clinical samples. Exemplary clinical samples that can be used in the diagnosis of infections are thus any samples which could possibly include nucleic acid, including samples from vaginal swabs and vaginal washes (Alderete et al., 1987b and Alderete et al., 1988c), urine or the like. A variety of hybridization techniques and systems are known which can be used in connection with the hybridization aspects of the invention, including diagnostic assays such as those described in Falkow et al., U.S. Pat. No. 4,358,535.

Accordingly, the nucleotide sequences of the invention are important for their ability to selectively form duplex molecules with complementary stretches of *T. vaginalis* gene segments. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15M–0.9M salt, at temperatures ranging from 20° C. to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, one will likely desire to employ an enzyme tag such as alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with pathogen nucleic acid-containing samples.

In general, it is envisioned that the hybridization probes described herein will be useful both as reagents in solution hybridization as well as in embodiments employing a solid phase. In embodiments involving a solid phase, the test DNA (or RNA) from suspected clinical samples, such as exudates, body fluids (e.g., amniotic fluid cerebrospinal fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

B. Host Cell Cultures and Vectors

In general, of course, prokaryotes are preferred for the initial cloning of DNA sequences and constructing the vectors useful in the invention. For example, in addition to the particular strains mentioned in the more specific disclosure below, on may mention by way of example, strains such as *E. coli*. K12 strain 294 (ATCC No. 31446), *E. coli* B, and *E. coli*×1776 (ATCC No. 31537). These examples are, of course, intended to be illustrative rather than limiting.

Prokaryotes may also be used for expression. The aforementioned strains, as well as *E. coli* W3110 (F-, lambda-, prototrophic, ATCC No. 273325), bacilli such as *Bacillus subtilus*, or other enterobacteriaceae such as *Salmonella typhimurium* or *Serratia marcesans*, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the microorganism for expression of its own proteins.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (Siebwenlist et al., 1980).

In addition to prokaryotes, eukaryotic microbes, such as yeast cultures may also be used. *Saccharomyces cerevisiase*, or common baker's yeast is the most commonly used among eukaryotic microorganisms, although a number of other strains are commonly available. For expression in Saccharomyces, the plasmid YRp7, for example, is commonly used (STinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters.are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

As origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

C. Immunoassays

It is proposed that the *T. vaginalis* proteins and peptides of the invention will find utility as immunogens in connection with vaccine development, as well as antigens in immunoassays for the detection of anti-*T. vaginalis*-reactive antibodies. This will include serum antibodies present in patients to the phenotypically varying immunogen, P270, or to the P55 protein uniquely expressed among the Type II isolates. Also, vaginal antibody can be envisioned to detect the P230 protein or fragments thereof.

Turning first to immunoassays, in their most simple and direct sense, preferred immunoassays of the invention include the various types of enzyme linked immunosorbent assays (ELISAs), immunoblot techniques, and the like, known to the art. However, it will be readily appreciated that utility is not limited to such assays, and useful embodiments include RIAs and other non-enzyme linked antibody binding assays or procedures.

In the preferred ELISA or immunoblot assay, peptides incorporating the *T. vaginalis* antigen sequences are immobilized onto a selected surface, preferably a surface exhibiting a protein affinity such as the wells of a polystyrene microtiter plate. After washing to remove incompletely adsorbed material, one will desire to bind or coat a nonspecific protein such as bovine serum albumin (BSA) or casein onto the well that is known to be antigenically neutral with regard to the test antisera. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological sample to be tested in a manner conducive to immune complex (antigen/antibody) formation. Such conditions preferably include diluting the antisera or clinical samples containing antibody with diluents such as BSA, bovine gamma globulin (BGG) and phosphate buffered saline (PBS)/Tween. These added reagents also tend to assist in the reduction of nonspecific background. The layered antisera or clinical sample is then allowed to incubate for from 2 to 4 hours, at temperatures preferably on the order of 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing, the occurrence and even amount of immunocomplex formation may be determined by subjecting same to a procedure designed to specifically detect the first antibody, such as the use of a labeled protein A or enzyme-conjugated second antibody having specificity for the first. Of course, in that the test sample will typically be of human origin, the second antibody will preferably be an antibody having specificity in general for human Ig. To provide a detecting means, the second antibody will preferably have an associated enzyme that will generate a color development upon incubating with an appropriate chromogenic substrate. Thus, for example, one will desire to contact and incubate the antibody-bound surface with a urease or peroxidase-conjugated anti-human Ig for a period of time and under conditions which favor the development of immunocomplex formation (e.g., incubation for 2 hours at room temperature in a PBS-containing solution such as PBS-Tween).

After incubation with the second antibody or protein A, enzyme-tagged or radiolabeled, and subsequent to washing to remove unbound material, the amount of label is quantified by incubation with a chromogenic substrate such as urea and bromocresol purple (e.g. where urease is enzyme tag) or 2,2'-azino-di-(3-ethyl-benzthiazoline-6-sulfonic acid [ABTS] and $H_2O_2$, where peroxidase is the enzyme label, or by measurement of radioactivity, where radiolabel is used. Quantification is then achieved by measuring the degree of color generation or radioactivity, e.g., using a visible spectra spectrophotometer or scintillation spectroscopy.

D. Vaccine Preparation and Use

Immunogenic compositions, believed to be suitable for use in the development of anti-trichomonal vaccines, may be prepared most readily directly from immunogenic proteins and/or peptides prepared as disclosed herein. Preferably the purified material is also extensively dialyzed to remove undesired small molecular weight molecules and/or lyophilization of the thus purified material for more ready formulation into a desired vehicle.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C.

for 30 second to 2 minute periods respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

E. Site-Specific Mutagenesis

Site-specific mutagenesis is a technique useful in the preparation of individual peptides, or biologically functional equivalent proteins or peptides, derived from the particular antigen sequence, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art (Geisselsoder et al., 1987; Kunkel et al., 1987). As will be appreciated, the technique typically employs a phage vector which exists in both a single stranded and double stranded form. Typical vectors useful in site-directed mutagenesis include vectors such as the M13 phage, for example, as disclosed by Messing et al., 1981. These phage are readily commercially available and their use is generally well known to those skilled in the art.

In general, site-directed mutagenesis in accordance herewith is performed by first obtaining a single-stranded vector which includes within its sequence a DNA sequence which encodes the desired antigen. An oligonucleotide primer bearing the desired mutated sequence is prepared, generally synthetically, for example by the method of Crea et al., 1978. This primer is then annealed with the singled-stranded vector, and subjected to DNA polymerizing enzymes, such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as *E. coli* cells and clones are selected which include recombinant vectors bearing the mutated sequence arrangement.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundency, changes can be made in the underlying DNA sequence without affecting the protein sequence. Moreover, due to considerations of biological functional equivalency, certain changes can be made in protein structure without affecting in kind or amount of the biological action or immunological reactivity. All such modifications are intended to be included within the scope of the appended claims.

REFERENCES

The following references are hereby incorporated by reference, for the reasons indicated in the foregoing specification.

Ackers, J. 1982. Immunology of amebas, giardia, and trichomoniasis. Viruses and Parasites; Immunodiagnosis and Prevention of Infectious Diseases. Plenum Publishing Corp., New York.

Alderete, J. F. 1983a. Antigenic analysis of several pathogenic strains of *Trichomonas vaginalis*. Infect. Immun. 39:1041–1047.

Alderete, J. F. 1983b. Identification of immunogenic and antibody-binding proteins on the membrane of pathogenic *Trichomonas vaginalis*. Infect Immun. 40:284–291.

Alderete, J. F., and E. Pearlman. 1983c. Pathogenic *Trichomonas vaginalis* cytotoxicity to cell culture monolayers. Brit. J. Vener. Dis. 60:99–105.

Alderete, J. F. 1984. Enzyme-linked immunosorbent assay for detection of antibody to *Trichomonas vaginalis*: Use of whole cells and aqueous extract as antigen. Brit. J. Vener. Dis. 60:164.

Alderete, J. F. and G. E. Garza. 1985a. Specific nature of *Trichomonas vaginalis* parasitism of host cell surfaces. Infect. Immun. 50:701–708.

Alderete, J. F., L. Suprun-Brown, L. Kasmala, J. Smith and M. Spence. 1985b. Heterogeneity of *Trichomonas vaginalis* and discrimination among trichomonal isolates and subpopulations by sera of patients and experimentally infected mice. Infect. Immun. 49:463–468.

Alderete, J. F., G. E. Garza, J. Smith, and M. Spence. 1986a. *Trichomonas vaginalis*: Electrophoretic analysis reveals heterogeneity among isolates due to high molecular weight trichomonad proteins. Exp. Parasitol. 61:244–251.

Alderete, J. F. and L. Kasmala. 1986b; Monoclonal antibody to a major glycoprotein immunogen mediates differential complement independent lysis of *Trichomonas vaginalis*. Infect. Immun. 53:697–699.

Alderete, J. F., L. Kasmala, E. C. Metcalfe, and G. E. Garza. 1986c. Phenotypic variation and diversity among *Trichomonas vaginalis* and correlation of phenotype with contact-dependent host cell cytotoxicity. Infect. Immun. 53:285–293.

Alderete, J. F., L. Suprun-Brown, and L. Kasmala. 1986d. Monoclonal antibody to a major surface immunogen differentiates isolates and subpopulations of *Trichomonas vaginalis*. Infect. Immun. 52:70–75.

Alderete, J. F. 1987a. *Trichomonas vaginalis* phenotypic variation may be coordinated for a repertoire or trichomonad surface immunogens. Infect. Immun. 55:1957–1962.

Alderete, J. F., P. Demeš, A. Gombošova, M. Valent, A. Jano ška, H. Fabušova, L. Kasmala, and E. C. Metcalfe. 1987b. Phenotype and protein/epitope phenotypic variation among fresh isolates of *Trichomonas vaginalis*. Infect. Immun. 55:1037–1041.

Alderete, J. F. 1988a. Alternating phenotypic expression of two classes of *Trichomonas vaginalis* surface markers. Rev. Infect. Dis. 10:S408–S412.

Alderete, J. F. and G. E. Garza. 1988b. Identification and properties of *Trichomonas vaginalis* proteins involved in cytadherence. Infect. Immun. 56:28–33.

Alderete, J. F., P. Demeš, A. Gombošova, M. Valent, M. Fabušsova, A. Janoška, J. Stefanovic, and R. Arroyo. 1988c. Specific parasitism by *Trichomonas vaginalis* of purified vaginal epithelial cells. Infect. Immun. 56:2558–2562.

Alderete, J. F. and K. A. Neale. 1989. Relatedness of major immunogen among all *Trichomonas vaginalis* isolates. Infect. Immun. 56:1849–1853.

Alderete, J. F., J. C. Boothroyd, D. C. Dailey, and J. P. McKay. 1990. Identification of a differentially regulated gene from *Trichomonas vaginalis* isolates which undergo phenotypic variation. Annual Meetings of the American Society for Microbiology. Anaheim, Calif.

Bolivar et al. 1977. Gene 2:95.

Bonner, W. M., and R. A. Laskey. 1974. A film detection method for tritium-labeled proteins and nucleic acids in polyacrylamide gels. Eur. J. Biochem. 46:83.

Burnette, W. N. 1981. Western Blotting: Electrophoretic Transfer of proteins from sodium dodecyl nitrocellulose and radiographic detection with antibody and radioiodinated protein. A. Anal. Biochem. 112:195.

Chang et al. 1978. Nature. 375:615.

Chirgwin, J. M., A. E. Przybyla, R. MacDonald, and W. J. Rutter. 1979. Isolation of biologically active ribonucleic acid from sources enriched in ribonuclease. Biochem. 18:5294–5299.

Chulay, J. D., J. A. Lyon, J. D. Haynes, A. I. Meierovics, C. T. Atkinson, and M. Aikawa. 1987. Monoclonal antibody characterization of *Plasmodium falciparum* antigens in immune complexes formed when shizonts rupture in the presence of immune serum. J. Immunol. 139:2768–2774.

Coombs, G. H. and M. J. North. 1983. An analysis of the proeeinases of *Trichomonas vaginalis* by acrylamide gel electrophoresis. Parasitol. 86:1–6.

Crea et al. 1978. Proc. Natl. Acad. Sci. U.S.A. 75:5765.

Diamond L. S. 1957. The establishment of various trichomonads of animals and man in axenic cultures. J Parasitol. 43:488–90.

Dintzis, R. Z., M. H. Middleton, and H. M. Dintzis. 1983. Studies on the immunogenicity and tolerogenicity of T-independent antigens. J. Immunol. 131:2196–2203.

Fiers et al. 1978. Nature 273:113.

Geisselsoder, J., F. Witney, and P. Yuckenberg. 1987. Efficient site-directed in vitro mutagenesis. BioTechniques. 5:787–791. Goeddel et al. 1979. Nature 281:544.

Goeddel et al. 1980. Nucleic Acids Res. 8:4057.

Hess et al. 1968. J. Adv. Enzyme Reg. 7:149.

Hitzeman et al. 1980. J. Biol. Chem. 255:2073.

Holland et al. 1978. Biochemistry 17:4900.

Honigberg, B. M., M. C. Livingston, and J. K. Frost. 1966. Pathogenicity of fresh isolates of *Trichomonas vaginalis*: "the mouse assay" versus clinical and pathologic findings. Acta Cytol. 10:353–361.

Hopp, T. P. and K. R. Woods. 1981. Prediction of protein antigenic determinants from amino acid sequence. Proc. Natl. Acad. Sci. U.S.A. 78:3824–3828.

Huynh, T. V., R. A. Young, and R. W. Davis. 1985. Constructing and Screening cDNA libraries in λgt11. In DNA Cloning: a practical approach. D. M. Glover (ed.). IRL Press, Washington.

Itakura et al. 1977. Science 198:1056.

Jones. 1977. Genetics 85:12.

Kemp, D. J., A. F. Couman, and D. Walliker. 1990. Genetic diversity in *Plasmodium falciparum*. Adv. Parasitol. 29:75–128.

Kingsman et al. 1979. Gene 7:141.

Kott, H. and S. Adler. 1961. The serological study of *Trichomonas sp.* parasitic in man. Trans. R. Soc. Trop. Med. Hyg. 55:333–344.

Krieger, J. N. 1981. Urologic aspects of trichomoniasis. Invest. Urol. 18:411–417.

Krieger, J. N., K. K. Holmes, M. R. Spence, M. F. Rein, W. M. McCormack, and M. R. Tam. 1985. Geographic variation among isolates of *Trichomonas vaginalis*: demonstration of antigenic heterogeneity by using monoclonal antibodies and the indirect immunofluorescence technique. J. Infect. Dis. 152:979–984.

Krieger, J. N., P. Wolner-Hanssen, C. Stevens, and K. K. Holmes. 1990. Characteristics of *Trichomonas vaginalis* isolates from women with and without colpitis macularis. J. Infect. Dis. 161:307–311.

Kunkel, T. A., J. D. Roberts, and R. A. Zakour. 1987. Rapid and efficient site-specific mutagenesis without phenotype selection. Methods Enzymol. 154:367–382. Laemmli, U. K. 1970. Cleavage of structural proteins during the assembly of the head of bacteriophage T4. Nature (London). 227:680.

Laga, M., H. Nzila, A. T. Manoka, M. Kivuvu, F. Behets, B. Edidi, P. Piot, and R. Ryder. 1989. High prevalence and incidence of HIV and other sexually transmitted diseases (STD) among 801 Kinshasa prostitutes. Abstracts of the V International Conference on AIDS, Montreal, Canada.

Laga, M., N. Nzila, A. T. Manoka, A. M. Malela, T. J. Bush, F. Behets, and W. L. Heyward. 1990. Non ulcerative sexually transmitted diseases (STD) as risk factors for HIV infection. Abstracts of the VI International Conference on AIDS, San Francisco, Calif.

Lockwood, B. C., M. J. North, K. I. Scott, A. F. Bremner, and G. H. Coombs, 1987. The use of a highly sensitive electrophoretic method to compare the proteinases of trichomonads. Mol. Biochem. Parasitol. 24:89–95.

Maniatis, T., E. F. Fritsch, and J. Sambrook. 1982. Molecular Cloning, A Laboratory Manual. Cold Spring Harbor Laboratory, New York.

Messing et al. 1981. Third Cleveland Symposium on Macromolecules and Recombinant DNA, Editor A. Walton, Elsevier, Amsterdam.

Masin, U., J. Coleman, and M. Inouze. 1983. Multiple expression cloning vehicle in *Escherichia coli.*, In Experimental Manipulation of Gene Expression. Academic Press, Inc. London.

Müller, M. 1983. *Trichomonas vaginalis* and other sexually transmitted Protozoan infections. International Perspectives of Neglected Sexually Transmitted Diseases. Hemisphere Publishing Corp., New York.

Neale, K. A. and J. F. Alderete. 1990. Analysis of the proteinases of representative *Trichomonas vaginalis* isolates. Infect. Immun. 58:157–162.

Peterson, K. M., and J. F. Alderete. 1982. Host plasma proteins on the surface of pathogenic *trichomonas vaginalis*. Infect Immun. 37:755–762.

Rein, M. F., and T. A. Chapel. 1975. Trichomoniasis, candidiasis, and the minor venereal diseases. Clin. Obstet. Gynecol. 18:73–88.

Siebwenlist et al. 1980. Cell 20:269.

Spence, M. R., D. H. Hollander, J. Smith, L. McCraig, D. Sewel, and M. Brockman. 1980. The clinical and laboratory diagnosis of *Trichomonas vaginalis* infection. Sex. Trans. Dis. 7:168–171.

Stinchcomb et al. 1979. Nature 282:39.

Su-Lin, K. E., and B. M. Honigberg. 1983. Antigenic analysis of *Trichomonas vaginalis* strains by quantitative fluorescent antibody methods. Z. Parasitenkd. 69:161–181.

Teras, J. K. 1966. Difference in the antigenic properties within strains of *Trichomonas vaginalis*. Wiad. Parazytol. 12:357–363.

Tissue Culture. 1973. Academic Press. (eds.) Kruse and Patterson.

Tschemper et al. 1980. Gene 10:157.

Wang, A. A., and C. C. Wang. 1985. Isolation and characterization of DNA from *Trichomonas vaginalis* and *Trichomonas foetus*. Molec. Biochem. Paraitol. 14:323–335.

Yanisch-Perron, C., J. Vieira, and J. Messing. 1985. Improved M13 phage cloning vectors and host strains: nucleotide sequences of the M13mp18 and pUC19 vectors. Gene 33:103.

---

What is claimed is:

1. An isolated DNA segment encoding all or part of an endogenous *Trichomonas vaginalis* P270 protein, wherein said DNA segment comprises a region encoding a DREGRD peptide epitope that is expressed during phenotypic variation in a type II *Trichomonas vaginalis* isolate.

2. A DNA segment of claim 1 that encodes a peptide region of an endogenous *Trichomonas vaginalis* P270 protein having one or more occurrences of the DREGRD epitope.

3. A DNA segment of claim 1 that encodes an entire, endogenous, *Trichomonas vaginalis* P270 protein having one or more occurrences of the DREGRD epitope.

4. An isolated polynucleotide comprising a base sequence that is identical or complementary to a segment of 25 or more contiguous bases of SEQ ID NO:1 or SEQ ID NO:3.

5. The isolated polynucleotide of claim 4, wherein the polynucleotide comprises a base sequence that is identical or complementary to a segment of 25 or more contiguous bases of SEQ ID NO:1.

6. The isolated polynucleotide of claim 4, wherein the polynucleotide comprises a base sequence that is identical or complementary to a segment of 25 or more contiguous bases of SEQ ID NO:3.

7. The isolated polynucleotide of claim 4, wherein the polynucleotide encodes the polypeptide of SEQ ID NO:2.

8. The isolated polynucleotide of claim 4, wherein the polynucleotide encodes the polypeptide of SEQ ID NO:4.

9. The isolated polynucleotide of claim 4, wherein the polynucleotide encodes a DREGRD peptide epitope.

10. A recombinant vector comprising a DNA segment in accordance with claim 1.

11. The recombinant vector of claim 10, further defined as a bacteriophage vector.

12. A transformed host cell which comprises a recombinant vector in accordance with claim 10, or a DNA segment in accordance with claim 1.

13. The transformed host cell of claim 12, further defined as a bacterial host cell.

14. A method for the preparation of a recombinant host cell comprising a DNA segment which encodes all or part of a protein expressed essentially only in a Type II *Trichomonas vaginalis* isolate and not in a Type I isolate, or a protein expressed essentially only in a Type I isolate but not in a Type II isolate, the method comprising the steps of:

a) preparing a recombinant clone bank comprised of individual colonies of recombinant host cells which include *Trichomonas vaginalis* DNA segments;

b) screening said bank by differential hybridization with a first probe set of nucleic acid sequences complementary to sequences expressed in Type II isolates, and a second probe set of nucleic acid sequences complementary to sequences expressed in Type I isolates, to identify a clone which comprises a DNA segment encoding all or part of a protein expressed essentially only in a Type II *Trichomonas vaginalis* isolate and not in a Type I isolate, or all or part of a protein expressed essentially only in a Type I isolate but not in a Type II isolate; and c) selecting and cultivating said identified clone.

15. The method of claim 14, wherein said clone expresses the protein or peptide.

16. A recombinant clone bank prepared according to steps (a) and (b) of claim 14 comprising one or more host cells transformed with segments of endogenous *Trichomonas vaginalis* DNA encoding proteins, or portions of proteins, expressed essentially only in a Type II *Trichomonas vaginalis* isolate.

17. A recombinant clone bank prepared according to steps (a) and (b) of claim 14 comprising one or more host cells transformed with segments of endogenous *Trichomonas vaginalis* DNA encoding proteins, or portions of proteins, expressed essentially only in a Type I *Trichomonas vaginalis* isolate.

18. The clone bank of claim 17, wherein the *Trichomonas vaginalis* DNA is comprised within a recombinant vector.

19. The clone bank of claim 18, wherein the recombinant vector is a plasmid.

20. The clone bank of claim 18, wherein the recombinant vector is a bacteriophage.

21. The clone bank of claim 16, wherein the recombinant host cells are recombinant bacterial cells.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 396 base pairs [DNA of Figure 2]
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GAATTC  CGG  GAT  AAC  GTT  AGA  AGT  AAA  GGA  GTC  ACA  TTA  CGC  GCA  GCA              48

CAA  CAA  GGA  CCA  CCA  TCC  ATT  AGC  GAT  TTT  ACA  ATA  GAA  GGT  GGC  ACA            96

GAA  CTG  ACA  ATT  GGT  AAT  ACA  TAT  CCA  ATC  ACT  ATC  ACA  CTT  TCG  CCA           144
```

```
TCA  TCA  GAT  TTA  GCA  GAT  TGC  TTT  TAT  GCT  TTC  GAC  ACA  GAA  ACT  CAG         192

CAT  ACA  TTC  CCA  GGT  GAT  GCT  GCC  AGT  AAA  AGC  CAG  TGC  ACA  GAA  CTA         240

TTG  GGT  AAC  TCT  GAT  AAA  ACA  GAG  TAT  ACA  GCC  AAA  TTA  CAA  GCT  TCC         288

GGT  TCT  GCA  GGC  AGT  TTC  AAT  CTT  TTC  ATC  CAA  GTT  GTT  GAT  AGA  GAA         336

GGT  AGG  GAT  AAC  GTT  AGA  AGT  AAA  GGA  GTC  ACA  TTA  CGC  GCA  GCA  CAA         384

CAA  GGG  GAATTC                                                                        396
```

( 2 ) INFORMATION FOR SEQ ID NO:2:

( i ) SEQUENCE CHARACTERISTICS:
        ( A ) LENGTH: 128 amino acids [amino acid of Figure 2]
        ( B ) TYPE: amino acids
        ( C ) STRANDEDNESS: single
        ( D ) TOPOLOGY: linear ( x i ) SEQUENCE DESCRIPTION: SEQ ID NO:2:

```
Arg  Asp  Asn  Val  Arg  Ser  Lys  Gly  Val  Thr  Leu  Arg  Ala  Ala  Gln  Gln
 1              5                        10                       15

Gly  Pro  Pro  Ser  Ile  Ser  Asp  Phe  Thr  Ile  Glu  Gly  Gly  Thr  Glu  Leu
               20                       25                       30

Thr  Ile  Gly  Asn  Thr  Tyr  Pro  Ile  Thr  Ile  Thr  Leu  Ser  Pro  Ser  Ser
          35                        40                       45

Asp  Leu  Ala  Asp  Cys  Phe  Tyr  Ala  Phe  Asp  Thr  Glu  Thr  Gln  His  Thr
     50                        55                       60

Phe  Pro  Gly  Asp  Ala  Ala  Ser  Lys  Ser  Gln  Cys  Thr  Glu  Leu  Leu  Gly
 65                       70                       75                       80

Asn  Ser  Asp  Lys  Thr  Glu  Tyr  Thr  Ala  Lys  Leu  Gln  Ala  Ser  Gly  Ser
                    85                       90                       95

Ala  Gly  Ser  Phe  Asn  Leu  Phe  Ile  Gln  Val  Val  Asp  Arg  Glu  Gly  Arg
               100                      105                      110

Asp  Asn  Val  Arg  Ser  Lys  Gly  Val  Thr  Leu  Arg  Ala  Ala  Gln  Gln  Gly
               115                      120                      125
```

( 2 ) INFORMATION FOR SEQ ID NO:3:

( i ) SEQUENCE CHARACTERISTICS:
        ( A ) LENGTH: 339 base pairs [DNA of Figure 5]
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
AA   GCT  TCC  GGT  TCT  GCA  GGC  AGT  TTC  AAT  CTT  TTC  ATC  CAA  GTT  GTT         47

GAT  AGA  GAA  GGT  AGG  GAT  AAC  GTT  AGA  AGT  AAA  GGA  GTC  ACA  TTA  CGC         95

GCA  GCA  CAA  CAA  GGA  CCA  CCA  TCC  ATT  AGC  GAT  TTT  ACA  ATA  GAA  GGT        143

GGC  ACA  GAA  CTG  ACA  ATT  GGT  AAT  ACA  TAT  CCA  ATC  ACT  ATC  ACA  CTT        191

TCG  CCA  TCA  TCA  GAT  TTA  GCA  GAT  TGC  TTT  TAT  GCT  TTC  GAC  ACA  GAA        239

ACT  CAG  CAT  ACA  TTC  CCA  GGT  GAT  GCT  GCC  AGT  AAA  AGC  CAG  TGC  ACA        287

GAA  CTA  TTG  GGT  AAC  TCT  GAT  AAA  ACA  GAG  TAT  ACA  GCC  AAA  TTA  CAA        335

GCT  T                                                                                  339
```

( 2 ) INFORMATION FOR SEQ ID NO:4:

( i ) SEQUENCE CHARACTERISTICS:
        ( A ) LENGTH: 112 amino acids [amino acid of Figure 5]
        ( B ) TYPE: amino acids ( C ) STRANDEDNESS: single
( D ) TOPOLOGY: linear ( x i ) SEQUENCE DESCRIPTION: SEQ ID NO:4:

| Ala | Ser | Gly | Ser | Ala | Gly | Ser | Phe | Asn | Leu | Phe | Ile | Gln | Val | Val | Asp |
|---|---|---|---|---|---|---|---|---|---|---|---|---|---|---|---|
| 1 | | | | 5 | | | | | 10 | | | | | 15 | |
| Arg | Glu | Gly | Arg | Asp | Asn | Val | Arg | Ser | Lys | Gly | Val | Thr | Leu | Arg | Ala |
| | | | 20 | | | | | 25 | | | | | 30 | | |
| Ala | Gln | Gln | Gly | Pro | Pro | Ser | Ile | Ser | Asp | Phe | Thr | Ile | Glu | Gly | Gly |
| | | 35 | | | | | 40 | | | | | 45 | | | |
| Thr | Glu | Leu | Thr | Ile | Gly | Asn | Thr | Tyr | Pro | Ile | Thr | Ile | Thr | Leu | Ser |
| | 50 | | | | | 55 | | | | | 60 | | | | |
| Pro | Ser | Ser | Asp | Leu | Ala | Asp | Cys | Phe | Tyr | Ala | Phe | Asp | Thr | Glu | Thr |
| 65 | | | | | 70 | | | | | 75 | | | | | 80 |
| Gln | His | Thr | Phe | Pro | Gly | Asp | Ala | Ala | Ser | Lys | Ser | Gln | Cys | Thr | Glu |
| | | | | 85 | | | | | 90 | | | | | 95 | |
| Leu | Leu | Gly | Asn | Ser | Asp | Lys | Thr | Glu | Tyr | Thr | Ala | Lys | Leu | Gln | Ala |
| | | | 100 | | | | | 105 | | | | | 110 | | |